United States Patent
Brown et al.

(10) Patent No.: US 9,701,719 B2
(45) Date of Patent: Jul. 11, 2017

(54) ATTENUATED CHIKUNGUNYA VIRUS

(71) Applicant: Research Development Foundation, Carson City, NV (US)

(72) Inventors: Dennis T. Brown, Raleigh, NC (US); Raquel Hernandez, Raleigh, NC (US)

(73) Assignee: Research Development Foundation, Carson City, NV (US)

( * ) Notice: Subject to any disclaimer, the term of this patent is extended or adjusted under 35 U.S.C. 154(b) by 234 days.

(21) Appl. No.: 14/038,545

(22) Filed: Sep. 26, 2013

(65) Prior Publication Data

US 2014/0086953 A1    Mar. 27, 2014

Related U.S. Application Data

(60) Provisional application No. 61/706,589, filed on Sep. 27, 2012.

(51) Int. Cl.
  *C07K 14/005* (2006.01)
  *A61K 38/00* (2006.01)
  *C07K 7/00* (2006.01)

(52) U.S. Cl.
  CPC ........... *C07K 14/005* (2013.01); *A61K 38/00* (2013.01); *C07K 7/00* (2013.01); *C12N 2770/36122* (2013.01); *C12N 2770/36134* (2013.01)

(58) Field of Classification Search
  None
  See application file for complete search history.

(56) References Cited

U.S. PATENT DOCUMENTS

| 6,306,401 | B1 | 10/2001 | Brown et al. |
| 7,128,915 | B2 | 10/2006 | Hernandez et al. |
| 7,335,363 | B2 | 2/2008 | Hernandez et al. |
| 2011/0236421 | A1 | 9/2011 | Brown et al. |
| 2012/0003255 | A1 | 1/2012 | Brown et al. |
| 2012/0003266 | A1* | 1/2012 | Nable et al. ............... 424/218.1 |

FOREIGN PATENT DOCUMENTS

WO    WO 2007/105111    9/2007

OTHER PUBLICATIONS

NP_690589, Structural polyprotein [chikungunya virus], Apr. 28, 2010.*
GenBank Accession # AAU43881, structural polyprotein [Chikungunya virus], 2005.*
Metz, et al., "Functional processing and secretion of Chikungunya virus E1 and E2 glycoprotein in insect cells," *Virology Journal*, 8(1):353-364, 2011.
PCT International Search Report and Written Opinion, issued in PCT Application PCT/US2013/061918 on Nov. 15, 2013.
Piper, et al., "Chikungunya Virus Host Range E2 Transmembrane Deletion Mutants Induce Protective Immunity against Challenge in C57BL/6J Mice," *Journal of Virology*, 87(12):6748-6757, 2013.

* cited by examiner

*Primary Examiner* — Benjamin P Blumel
(74) *Attorney, Agent, or Firm* — Parker Highlander PLLC

(57) ABSTRACT

Novel attenuating deletions of Chikungunya virus E2 polypeptides are provided as are attenuated viruses comprising the deletions. Also provided are immunogenic compositions comprising the attenuated viruses and methods of producing such viruses in cells (such as insect cells). Viruses of the embodiments can be used for immunization of animals to provide protection from the pathogenic effects of Chikungunya virus infection.

15 Claims, 4 Drawing Sheets

US 9,701,719 B2

ATTENUATED CHIKUNGUNYA VIRUS

This application claims the benefit of U.S. Provisional Patent Application No. 61/706,589, filed Sep. 27, 2012, which is incorporated herein by reference in its entirety.

INCORPORATION OF SEQUENCE LISTING

The sequence listing that is contained in the file named "CLFR.P0397US_ST25.txt", which is 99 KB (as measured in Microsoft Windows®) and was created on Sep. 26, 2013, is filed herewith by electronic submission and is incorporated by reference herein.

BACKGROUND OF THE INVENTION

1. Field of the Invention

The present invention relates generally to the field of molecular biology and virology. More particularly, it concerns Chikungunya polypeptides and viruses that are attenuated in mammalian hosts.

2. Description of Related Art

Chikungunya virus (ChikV is a member of the Togaviridae family; genus *Alphavirus* (Khan et al., 2002) and is pathogenic to humans. ChikV is an arthropod borne virus (arbovirus) spread by the bite of an aedene mosquito. As with all alphaviruses its genome is composed of a small ~11 Kb plus polarity single-stranded RNA. The genome encodes 3 structural proteins, E1, E2, and C and 4 nonstructural proteins nsP1-4. As a member of the Togaviruses these viruses are enveloped and as arboviruses they contain a membrane envelope derived from the insect or vertebrate host. The alphavirus genus contains 29 known species which cause encephalitis, fever, and/or arthralgia.

ChikV was first isolated from the blood of a febrile patient in Tanzania in 1953 where the virus was endemic (Pialoux et al., 2007). Outbreaks occur repeatedly in west, central, and southern Africa and have caused several human epidemics in those areas since that time. However, ChikV is a re-emerging pathogenic virus and is now also endemic in south east Asia (see, e.g., the world wide web at searo.who.int/index.htm). Recently, ChikV spread from Asia and the Indian Ocean to Italy (Rezza et al. 2007; Mavalankar et al. 2008). Of the two strain lineages of ChikV, the African; remains enzootic by cycling between mosquitoes and monkeys but the Asian strain is transmitted directly between mosquitoes and humans. This cycle of transmission may have allowed the virus to become more pathogenic as the reservoir host was eliminated (Powers et al., 2000).

In humans, ChikV causes a debilitating disease characterized by fever, headache, nausea, vomiting, fatigue, rash, muscle pain and joint pain; the symptoms commonly associated with Dengue virus infection (with the exception of the arthralgia). Incubation can be 2-12 days, but most commonly 3-7 days with "silent" infections occurring with unknown frequency (WHO, Weekly epidemiological record. 2007). ChikV can be transmitted from mother to child (Ramful et al. 2007) and can produce chronic persisting symptoms including crippling arthralgia, encephalitis and myocarditis (rare) (Paul et al. 2011). ChikV epidemics from 2004-2011 have resulted in 1.4-6.5 million reported cases, with imported cases to 40 countries (Suhrbier et al. 2012). *Aedes aegypti* is the primary vector of ChikV, but recent outbreaks, which involved mortalities, have been propagated through the *Aedes albopictus* mosquito (Mavalankar et al. 2008; Dubrulle et al. 2009). Importantly, this mosquito vector has spread to 12 European countries as well as to the Australian continent (Johnson et al. 2008). Despite significant morbidity and mortality associated with ChikV infections and its growing prevalence and geographic distribution there is currently no vaccine or antiviral for ChikV approved for human use (Barrett et al. 2009).

SUMMARY OF THE INVENTION

Embodiments of the invention concern recombinant Chikungunya virus E2 polypeptides comprising amino acid deletions in the transmembrane domain. For example, a recombinant E2 polypeptide comprising the deletion can be efficiently expressed on insect cell membranes, but cannot be efficiently expressed in mammalian cell membranes. Accordingly, a recombinant Chikungunya virus comprising a deleted E2 of the embodiments efficiently replicates in insect cells, but inefficiently replicate in mammalian cells and are therefore highly attenuated relative to mammals.

Accordingly, in a first embodiment, there is provided a recombinant polypeptide wherein the polypeptide comprises an amino acid sequence at least 85% identical to a wild type Chikungunya virus E2 polypeptide and comprises a deletion in the transmembrane domain (TMD). In some aspects, the recombinant polypeptide is at least 90% identical to a Chikungunya virus E2 polypeptide from the West African strain 37997 (SEQ ID NO:1), India isolate RGCB699-09 (SEQ ID NO:9) or Maritius isolate BNI1446 (SEQ ID NO:11). In some aspects, a recombinant polypeptide is at least 91%, 92%, 93%, 94%, 95% or 96% identical to SEQ ID NO:1, 9 or 11. In preferred aspects a deletion in TMD according to the embodiments is a deletion of 8-11 amino acids in the TMD (which corresponds to amino acid positions 365-390 of SEQ ID NO:1). For example, the deletion can be a deletion of 8, 9, 10 or 11 amino acids in the TMD.

In certain specific aspects, a recombinant polypeptide of the embodiments comprises a deletion of 9 amino acids in the TMD. For example, the polypeptide can comprise a deletion of the amino acids corresponding to amino acid positions 372-380, 374-382 or 373-381 of SEQ ID NO: 1. Examples of such polypeptide include, without limitation, polypeptides comprising the amino acid sequence of SEQ ID NO:3, SEQ ID NO:5, SEQ ID NO:7 or a sequence at least 90% identical to the foregoing sequences. In a further aspect, a recombinant polypeptide of the embodiments comprises a deletion of 10 amino acids in the TMD. For example, the polypeptide can comprise a deletion of the amino acids corresponding to amino acid positions 372-381, 374-383 or 373-382 of SEQ ID NO:1. Examples of such a polypeptide include, without limitation, polypeptides comprising the amino acid sequence of SEQ ID NO:15, SEQ ID NO:17, SEQ ID NO:19 or a sequence at least 90% identical to the foregoing sequences.

In a further embodiment there is provided a polynucleotide molecule encoding a recombinant Chikungunya virus E2 polypeptide of the embodiments. For example, the polynucleotide can comprise a sequence at least 85%, 90%, 91%, 92%, 93%, 94%, 95%, 96% or 97% identical to a Chikungunya virus E2 coding sequence from the West African strain 37997 (SEQ ID NO:2), India isolate RGCB699-09 (SEQ ID NO:10) or Maritius isolate BNI1446 (SEQ ID NO:12). Thus, in some specific aspects, a polynucleotide of the embodiments comprises a sequence at least 90%, 91%, 92%, 93%, 94%, 95%, 96%, 97%, 98% or 99% to SEQ ID NO:4; SEQ ID NO:6; SEQ ID NO:8; SEQ ID NO:16; SEQ ID NO:18; or SEQ ID NO:20 (e.g., a sequence 100% identical to any of the foregoing sequences). A polynucleotide of the embodiments can be a DNA or RNA sequence, such as a Chikungunya virus E2 genomic RNA.

In still a further embodiment there is provided a host cell comprising a polypeptide or a polynucleotide of the embodiments. For example, the host cell can be a eukaryotic or prokaryotic cell. In certain aspects, the host cell is an insect cell, such as a *Spodoptera frugiperda* cell. Thus, in some aspects, a culture of insect cells (e.g., SF9 cells) is provided wherein the cells comprise a polypeptide and/or polynucleotide of the embodiments.

In still yet a further embodiment there is provided a recombinant virus particle comprising a polypeptide or polynucleotide of the embodiments. For example, in certain aspects, the viral genome comprises a polynucleotide sequence of the embodiments. In some aspects, a viral particle of the embodiments can be defined as a live attenuated Chikungunya virus. In further aspects, a recombinant virus comprises at least one additional attenuating mutation. For example, the additional attenuating mutation can be a deletion, insertion or substitution of one or more nucleotides in the viral genome. In certain aspects, the recombinant virus is adapted for growth insect cell, such as a virus that have been passaged 10 or more times in an insect cell line. In still yet further aspects a recombinant virus of the embodiments is inactivated or partially inactivated, for example by treatment with a chemical (e.g., formalin), with heat or with radiation.

As outlined above, in some aspects, a recombinant virus according to the embodiments can comprise one ore more additional attenuating mutations. For example, in some aspects, a Chikungunya virus coding sequence can comprise an internal ribosomal entry site of a encephalomyelocarditis virus substituted for the sequence encoding the 5' UTR of the viral subgenomic RNA (see, e.g., U.S. Pat. Publn. No. 20110052634, incorporated herein by reference).

In yet a further embodiment there is provided a method of producing a recombinant virus of the embodiments comprising (a) infecting a host cell with a recombinant virus and (b) collecting progeny virus from the host cell. In further aspects, a method of the embodiments can comprise, expressing viral genome (e.g., a genome comprising a polynucleotide of the embodiments) in a host cell and collecting virus particles produced by the host cell. In certain aspects the host cell is an insect cell, such as an SF9 cell.

In still further embodiments there is provided an immunogenic composition comprising a recombinant polypeptide, polynucleotide or virus particle of the embodiments in a pharmaceutically acceptable carrier. In preferred aspects, an immunogenic composition comprises a recombinant Chikungunya virus of the embodiments (e.g., a live attenuated Chikungunya virus). In further aspects, an immunogenic composition further comprises additional components such as an adjuvant, an immunomodulator, a preservative or a stabilizer. Thus, in some aspects, a composition is provided for use in preventing the symptoms of a Chikungunya virus infection, the composition comprising a recombinant virus particle of the embodiments in a pharmaceutically acceptable carrier.

In yet still a further embodiment there is provided a method of producing an immune response in a subject comprising administering an immunogenic composition of embodiments to the subject. For example, a method of the embodiments can be further defined as a method for preventing symptoms (e.g., fever, rash or virus-associated arthritis) of a Chikungunya virus infection in a subject. In still further aspects a method can be defined as a method for reducing the probability of a Chikungunya virus infection in a subject. In certain aspects, a subject is a subject who is at risk of acquiring a Chikungunya virus infection, such as a subject who lives in an endemic area or who lives in or has visited a region known to have circulating Chikungunya virus. In further aspects, a subject is a subject that is at risk for having severe symptoms from Chikungunya virus infection such as a subject who is immunosuppressed, elderly or who has arthritis. In preferred aspects, the subject is a human subject.

In further aspects, an immunogenic composition of the embodiments can be administered to a subject orally, intravenously, intramuscularly, intraperitoneally, intradermally or subcutaneously. For example, in some aspects, the composition is administered to a subject by an injection, e.g., an intramuscular or subcutaneous injection. In some cases, the composition is administered multiple times, such as 2, 3, 4 or 5 times. In certain cases, each administration is separated by a period of days, weeks, months or years.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

Figure 1:
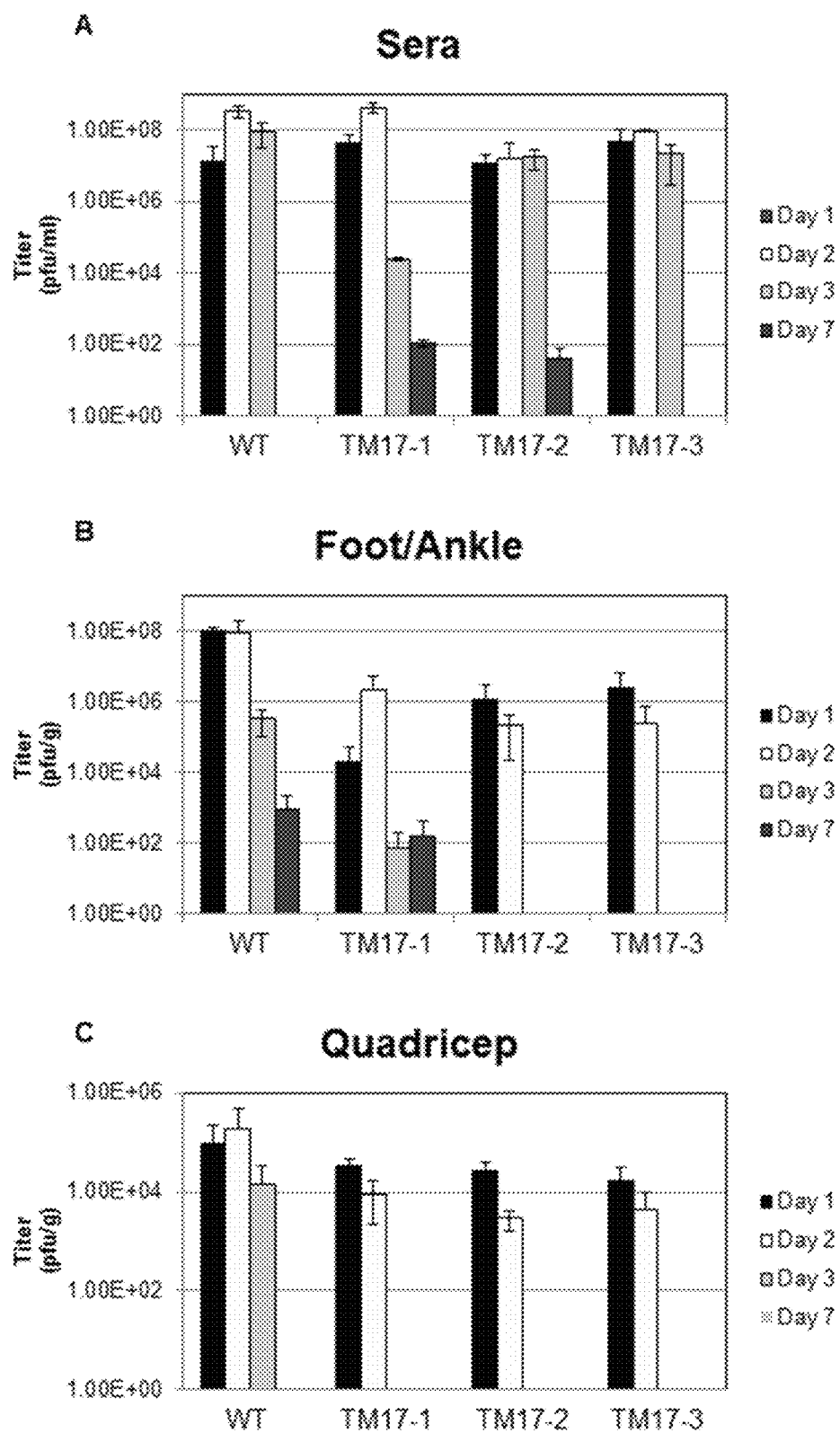
FIG. 1: Pre-challenge viremia by plaque assay in the designated tissues at 1, 2, 3, and 7 days after injection with $10^3$ pfu of ChikV, TM17-1, TM17-2, or TM17-3. The values of the mutant virus compared to the WT viremias were analyzed by students' t test and are noted where significant differences were found. In (A) the viremia detected in mouse sera is shown. Analysis of the titers shows no significant difference between the mutants and WT until day 2 for TM17-2, p<0.05, and day 3 p<0.001 for TM17-1. (B) Foot and ankle tissue titers differ from WT as follows: day 1 p<0.001 for TM17-1, p<0.01 TM-2, and on day 2; TM17-1, 2 and 3 were titers were significantly lower (p<0.05 respectively). One day 3 virus had been cleared from the TM17-2/3 infected mice. However, WT and TM17-1 had not been cleared from the foot/ankle at day 7. (C) The titers from quadriceps are shown. All the mutant viruses were cleared by day 3. No viremia was detected in mice injected with mock samples. Limit of detection of the plaque assay is 80 pfu.
Figure 2:
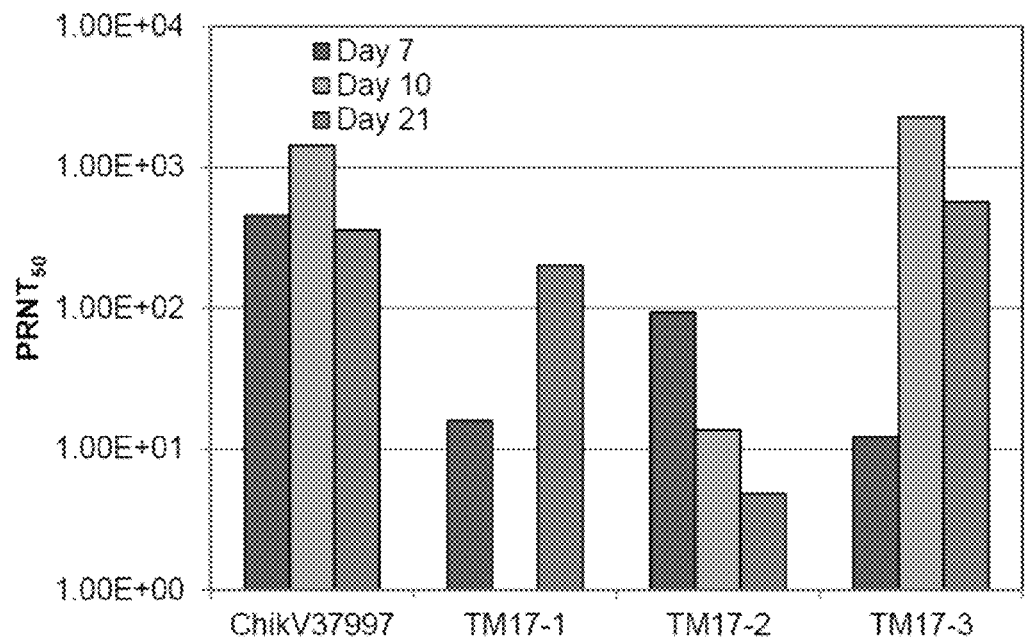
FIG. 2: Neutralizing antibody titers present in mouse sera 7, 10, and 21 days after injection (pre-challenge) with wild type or attenuated mutant ChikV37997. Titers shown represent the geometric means of sera from 3 different mice per group per day. Because of the variability of the data and the small group size, no significant differences could be established for the levels of NAb on these 3 days.

ChikV is a re-emerging human pathogen that has now established itself in south east Asia as well as Africa and has recently spread to Europe (Rezza et al. 2007; Mavalankar et al. 2008). In humans, ChikV causes a debilitating disease characterized by fever, headache, nausea, vomiting, fatigue, rash, muscle pain and joint pain. Human ChikV epidemics from 2004-2011 have resulted in 1.4-6.5 million reported cases, including a number of deaths. However, despite significant morbidity and mortality associated with ChikV infection and its growing prevalence and geographic distribution there is currently no vaccine or antiviral for ChikV approved for human use (Barrett et al. 2009). Thus, ChikV antigens and attenuated viruses are desperately needed for development of vaccines.

Embodiments of the invention address this need by providing deleted ChikV E2 polypeptides that render the virus highly attenuated in mammalian hosts. In particular, the studies detailed below demonstrate that ChikV expressing mutant E2 glycoproteins comprising a deletion of 9 or 10 amino acids in the transmembrane domain (e.g., the TM17 mutants) are highly attenuated and can serve as the basis for viral vaccine compositions. Importantly, large deletions, such as those studied, do not revert in vitro or in vivo (Smith et al. 2012). Moreover, though highly attenuated in mammalian cells, the viruses can be grown to near wild type titers in insect cells, thereby allowing for efficient production of vaccine strains. When injected into test animals the attenuated viruses were found to be safe, in that they did not persist in the blood or joints of the infected animals. The ChikV TM17-2 mutant, for example, did not produce any swelling at the site of injection, produced little if any inflammation in the foot/ankle or quad and did not persist in any tissue tested pre-challenge. Upon challenge of animals exposed to the mutant viruses with WT ChikV the animals were found to be protected from infection. In particular, ChikV TM17-2 provided significant protection against infection even as compared to TM 17-1 and WT ChikV. Assay of the serum, foot/ankle and quad post challenge did not detect any virus for mice infected with TM17-2. Considering that infection of humans with an arbovirus confers lifelong immunity, the ChikV TM17-2 protected better even than infection with WTChikV which allowed a transient infection post challenge.

The mutant viruses described here provide ideal vaccine candidates. First, they are high attenuated as demonstrated by their reduced replication efficiency in mammalian cells and the lack of persistence and symptoms of infection upon introduction into test animals. Second because of the large deletions that are used, the chance of reversion to wild type has been minimized. Most importantly, the viruses produce a robust and protective immune response. In fact certain mutant viruses such as TM17-2 produced an immune response that provides even greater protection that infection of animals with wild type virus. Together these studies have identified highly attenuated, non-reactogenic, and efficacious strains of ChikV which can (and should) be further developed for use in human vaccines.

II. Reference to the Sequence Listing

The following sequences are provided in the sequence listing and may be used in accordance with certain aspects of the embodiments.

SEQ ID NO:1—amino acid sequence for WT Chikungunya virus E2 polypeptide West African strain 37997 (Genbank #EU224270, incorporated herein by reference)

SEQ ID NO:2—polynucleotide sequence encoding SEQ ID NO:1 SEQ ID NO:3—amino acid sequence for Chikungunya virus E2 polypeptide "TM17-1"

SEQ ID NO:4—polynucleotide sequence encoding SEQ ID NO:3 SEQ ID NO:5—amino acid sequence for Chikungunya virus E2 polypeptide "TM17-2"

SEQ ID NO:6—polynucleotide sequence encoding SEQ ID NO:5 SEQ ID NO:7—amino acid sequence for Chikungunya virus E2 polypeptide "TM17-3"

SEQ ID NO:8—polynucleotide sequence encoding SEQ ID NO:7 SEQ ID NO:9—amino acid sequence for WT Chikungunya virus E2 polypeptide India isolate RGCB699-09 (Genbank #GU562827, incorporated herein by reference)

SEQ ID NO:10—polynucleotide sequence encoding SEQ ID NO:9

SEQ ID NO:11—amino acid sequence for WT Chikungunya virus E2 polypeptide Maritius isolate BNI1446 (Genbank #GU434106, incorporated herein by reference)

SEQ ID NO:12—polynucleotide sequence encoding SEQ ID NO:11

SEQ ID NO:13—TMD of Sindbis virus E2

SEQ ID NO:14—TMD of WT Chikungunya virus E2

SEQ ID NO:15—amino acid sequence for Chikungunya virus E2 polypeptide "TM16-1"
SEQ ID NO:16—polynucleotide sequence encoding SEQ ID NO:15
SEQ ID NO:17—amino acid sequence for Chikungunya virus E2 polypeptide "TM16-2"
SEQ ID NO:18—polynucleotide sequence encoding SEQ ID NO:17
SEQ ID NO:19—amino acid sequence for Chikungunya virus E2 polypeptide "TM16-3"
SEQ ID NO:20—polynucleotide sequence encoding SEQ ID NO:19
SEQ ID NO:21—Genomic polynucleotide sequence for WT Chikungunya virus, West African strain 37997
SEQ ID NO:22—Amino acid sequence for the non-structural polyprotein of WT Chikungunya virus, West African strain 37997
SEQ ID NO:23—Genomic polynucleotide sequence for the structural polyprotein of WT Chikungunya virus, West African strain 37997
SEQ ID NO:24-25—Synthetic oligonucleotide primers III. Recombinant Polypeptide and Polynucleotides The recombinant polypeptides and viruses of certain aspects of the embodiments are based on deletion mutations in the transmembrane domains of membrane glycoproteins of ChikV, in particular the ChikV EZ TMD. Like other viruses, the E2 membrane glycoprotein has a hydrophobic membrane-spanning domain which anchors the protein in the membrane bilayer (Rice et al., 1982). The membrane-spanning domain needs to be long enough to reach from one side of the bilayer to the other in order to hold or anchor the proteins in the membrane. Unlike mammalian cell membranes, the membranes of insect cells contain no cholesterol (Clayton 1964; Mitsuhashi et al., 1983). Because insects have no cholesterol in their membranes, the insect-generated viral membrane will be thinner in cross section than the viral membranes generated from mammals. Consequently, the membrane-spanning domains of proteins integrated into insect membranes do not need to be as long as those integrated into the membranes of mammals. Accordingly, as demonstrated for the first time here ChikV E2 polypeptides with a 8-11 amino acid deletion in their TMD result in viruses tat can replicate efficiently in insect cells but show reduced replication in mammalian cells that comprise thicker membranes. Further methods of modifying the a glycoprotein trans membrane domain are provided for instance in U.S. Pat. Nos. 6,306,401; 6,589,533; 7,128,915 and 7,335,363, each incorporated herein by reference.

In certain embodiments recombinant viruses or polypeptides according to the current embodiments may comprise two or more host range mutations or additionally comprise other mutations such as attenuating mutations, mutations to increase immunogenicity or viral stability or any mutations that may be used for vaccine production and that are current known in the art.

In additional aspects, recombinant polynucleotide, polypeptides or viruses of the embodiments can comprise additional deletions, substitutions or insertions (or amino acids or nucleic acids). For example, sequences from other ChikV strains can be incorporated into the recombinant molecules of the embodiments. Thus, in some aspects amino acid or nucleic acid changes can be made in molecules by substituting the position for a corresponding position from another strain of virus. Similarly, in the case of amino acid substitution, changes can be made with amino acids having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the E2 polypeptides described herein may be modified by the substitution of an amino acid, for different, but homologous amino acid with a similar hydrophilicity value. Amino acids with hydrophilicities within +/−1.0, or +/−0.5 points are considered homologous.

IV. Viral Vaccines

Certain aspects of the present invention are drawn to a method of producing an immunogenic composition or viral vaccine from genetically engineered membrane-enveloped viruses, such as Chikungunya virus, for vaccination of mammals, comprising the steps of introducing the engineered virus into insect cells and allowing the virus to replicate in the insect cells to produce a viral vaccine.

Certain aspects of the embodiments concern host-range mutant viruses. It is contemplated in certain aspects of the invention that one, two, three, four or more of these types of mutations can be combined, for example, to formulate a tetravalent vaccine. Furthermore, certain aspects of the present invention provide a method of producing a viral vaccine against a disease spread by a wild mosquito population to a mammal, comprising the steps of genetically engineering a mutation of one or more amino acids in a ChikV E2 protein such as the TMD to produce an engineered virus, wherein the transmembrane protein is able to span the membrane envelope when the virus replicates in mosquito cells, but is unable to efficiently span the membrane envelope when the virus replicates in mammalian cells, and wherein the virus remains capable of replicating in mosquito cells; introducing the engineered virus into a wild mosquito population; and allowing the virus to replicate in cells of the wild mosquito population to produce a population of mosquitoes which excludes the wild-type pathogenic virus and harbors the vaccine strain of the virus such that a mosquito bite delivers the vaccine to a mammal that is bitten.

In addition, certain aspects of the present invention provide a method of vaccinating an individual in need of such treatment, comprising the steps of introducing the viral vaccine of the present invention into the individual and allowing the vaccine to produce viral proteins for immune surveillance and to stimulate the immune system for antibody production in the individual.

A. Vaccine Preparations

In any case, a vaccine component (e.g., an antigenic peptide, polypeptide, nucleic acid encoding a proteinaceous composition, or virus particle) may be isolated and/or purified from the chemical synthesis reagents, cell, or cellular components. A vaccine component may be cultured in a population of cells, such as a cell line. Any suitable cell population or cell line may be used. For example, a vaccine component (e.g., a polypeptide, a nucleic acid encoding a polypeptide, or a virus particle) may be cultured in insect cells. Suitable insect cells include, but are not limited to, C6/36 cells, Sf9 cells, other Sf series cells, *drosophila* 51 cells, other *drosophila* cell lines, or TN368 cells. It is anticipated that any cultured insect cells may be used to grow the vaccine components or viruses disclosed herein.

The C6/36 cell line (derived from *Aedes albopictus*) is made up of mosquito cells and is frequently used to study arboviruses. C6/36 cells can be transfected with a vaccine component, such as a polypeptide or a nucleic acid encoding a polypeptide. The production of viruses can be visualized and monitored using a focus assay.

The Sf9 cell line (derived from *Spodoptera frugiperda*) is commonly used to express recombinant proteins and can be infected by viruses, including arboviruses. For example, Sf9 cells can be infected by viruses including recombinant baculovirus and St. Louis encephalitis, Yellow fever, DEN-1, DEN-2, Gumbo limbo, Eastern equine encephalomyelitis, herpes simplex virus type 1, and vesicular stromatitis viruses (Zhang et al., 1994). Yellow fever, DEN-1, and DEN-2 viruses can replicate in Sf9 cells (Zhang et al., 1994) such that Sf9 cells can be used to culture and produce such viruses. Likewise, Sf9 cells can be used use for production of the recombinant ChikV of the embodiments.

In a method of producing a vaccine component, purification is accomplished by any appropriate technique that is described herein or well known to those of skill in the art (e.g., Sambrook et al., 1987). Although preferred for use in certain embodiments, there is no general requirement that an antigenic composition of the present invention or other vaccine component always be provided in their most purified state. Indeed, it is contemplated that a less substantially purified vaccine component, which is nonetheless enriched in the desired compound, relative to the natural state, will have utility in certain embodiments, such as, for example, total recovery of protein product, or in maintaining the activity of an expressed protein. However, it is contemplated that inactive products also have utility in certain embodiments, such as, e.g., in determining antigenicity via antibody generation.

Certain aspects of the present invention also provide purified, and in preferred embodiments, substantially purified vaccines or vaccine components. The term "purified vaccine component" as used herein, is intended to refer to at least one vaccine component (e.g., a proteinaceous composition, isolatable from cells), wherein the component is purified to any degree relative to its naturally obtainable state, e.g., relative to its purity within a cellular extract or reagents of chemical synthesis. In certain aspects wherein the vaccine component is a proteinaceous composition, a purified vaccine component also refers to a wild-type or mutant protein, polypeptide, or peptide free from the environment in which it naturally occurs.

Where the term "substantially purified" is used, this will refer to a composition in which the specific compound (e.g., a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g., antigenicity), or assessing the number of polypeptides within a fraction by gel electrophoresis.

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s). For example, it is contemplated that immunomodulators can be included in the vaccine to augment a cell or a patient's (e.g., an animal's) response. Immunomodulators can be included as purified proteins, nucleic acids encoding immunomodulators, and/or cells that express immunomodulators in the vaccine composition.

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

Optionally, adjuvants that are known to those skilled in the art can be used in the administration of the viruses of the invention. Adjuvants that can be used to enhance the immunogenicity of the viruses include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In the case of a virus delivered via a mucosal route (for example, orally) mucosal adjuvants such as the heat-labile toxin of *E. coli* (LT) or mutant derivations of LT can be used as adjuvants. In addition, genes encoding cytokines that have adjuvant activities can be inserted into the viruses. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses.

An immunologic composition of the present invention may be mixed with one or more additional components (e.g., excipients, salts, etc.) that are pharmaceutically acceptable and compatible with at least one active ingredient (e.g., antigen). Suitable excipients are, for example, water, saline, dextrose, glycerol, ethanol and combinations thereof.

An immunologic composition of the present invention may be formulated into the vaccine as a neutral or salt form. A pharmaceutically acceptable salt, includes the acid addition salts (formed with the free amino groups of the peptide) and those that are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2 ethylamino ethanol, histidine, procaine, and combinations thereof.

In addition, if desired, an immunologic composition may comprise minor amounts of one or more auxiliary substances such as for example wetting or emulsifying agents, pH buffering agents, etc. that enhance the effectiveness of the antigenic composition or vaccine.

B. Vaccine Administration

Viruses of the embodiments can be administered as primary prophylactic agents in adults or children at risk of infection, or can be used as secondary agents for treating infected patients. Examples of patients who can be treated using the ChikV-related vaccines and methods of the invention include (i) children in areas in which ChikV is endemic, such as Asia, and Africa, (ii) foreign travelers, (iii) military personnel, and (iv) patients in areas of a ChikV epidemic. Moreover, inhabitants of regions where the disease has been observed to be expanding (e.g., Southern Europe), or regions where it may be observed to expand in the future (e.g., regions infested with *Aedes aegypti* or *Aedes albopictus*), can be treated according to the invention.

Formulation of viruses of the invention can be carried out using methods that are standard in the art. Numerous pharmaceutically acceptable solutions for use in vaccine preparation are well known and can readily be adapted for use in the present invention by those of skill in this art (see, e.g., Remington's Pharmaceutical Sciences, $18^{th}$ Ed., 1990). In two specific examples, the viruses are formulated in Minimum Essential Medium Earle's Salt (MEME) containing 7.5% lactose and 2.5% human serum albumin or MEME containing 10% sorbitol. However, the viruses can simply be diluted in a physiologically acceptable solution, such as sterile saline or sterile buffered saline. In another example, the viruses can be administered and formulated, for example, in the same manner as the yellow fever 17D vaccine, e.g., as a clarified suspension of infected chicken embryo tissue, or a fluid harvested from cell cultures infected with the chimeric yellow fever virus. Preferably, virus can be prepared or administered in FDA-approved insect cells.

The immunogenic compositions of the embodiments can be administered using methods that are well known in the art, and appropriate amounts of the vaccines administered can readily be determined by those of skill in the art. For example, the viruses of the invention can be formulated as sterile aqueous solutions containing between $10^2$ and $10^7$ infectious units (e.g., plaque-forming units or tissue culture infectious doses) in a dose volume of 0.1 to 1.0 ml, to be administered by, for example, intramuscular, subcutaneous, or intradermal routes. Further, the immunogenic compositions of the embodiments can be administered in a single dose or, optionally, administration can involve the use of a priming dose followed by a booster dose that is administered, e.g., 2-6 months later, as determined to be appropriate by those of skill in the art.

The manner of administration of an immunogenic compositions of the embodiments may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in creams, in lipid compositions (e.g., liposomes), or by other methods or any combination of the forgoing as would be known to one of ordinary skill in the art (see, for example, Remington's Pharmaceutical Sciences, $18^{th}$ Ed., 1990, incorporated herein by reference).

A vaccination schedule and dosages may be varied on a patient-by-patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

An immunogenic compositions of the embodiments is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1.5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed—and assays of protection from challenge with the ChikV—can be performed following immunization.

Certain aspects of the present invention include a method of enhancing the immune response in a subject comprising the steps of contacting one or more lymphocytes with a ChikV immunogenic composition, wherein the antigen comprises as part of its sequence a nucleic acid or amino acid sequence encoding mutant E2 protein, according to the invention, or an immunologically functional equivalent thereof. In certain embodiments the one or more lymphocytes is comprised in an animal, such as a human. In other embodiments, the lymphocyte(s) may be isolated from an animal or from a tissue (e.g., blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained from an animal (e.g., a patient), then pulsed with a composition comprising an antigenic composition. In a preferred embodiment, the lymphocyte(s) may be administered to the same or different animal (e.g., same or different donors).

C. Pharmaceutical Compositions

It is contemplated that pharmaceutical compositions may be prepared using the novel mutated viruses of certain aspects of the present invention. In such a case, the pharmaceutical composition comprises the novel virus and a pharmaceutically acceptable carrier. A person having ordinary skill in this art readily would be able to determine, without undue experimentation, the appropriate dosages and routes of administration of this viral vaccination compound. When used in vivo for therapy, the vaccine of certain aspects of the present invention is administered to the patient or an animal in therapeutically effective amounts, i.e., amounts that immunize the individual being treated from the disease associated with the particular virus. It may be administered parenterally, preferably intravenously or subcutaneously, but other routes of administration could be used as appropriate. The amount of vaccine administered may be in the range of about $10^3$ to about $10^6$ pfu/kg of subject weight. The schedule will be continued to optimize effectiveness while balancing negative effects of treatment (see Remington's Pharmaceutical Science, 18th Ed., (1990); Klaassen In: Goodman and Gilman's: The Pharmacological Basis of Therapeutics, $8^{th}$ Ed. (1990); which are incorporated herein by reference). For parenteral administration, the vaccine may be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods of the Studies

Biosafety

All studies involving viable ChikV were performed in certified BSL-3 laboratories in biosafety cabinets using biosafety protocols approved by the Institutional Biosafety Committee of North Carolina State University. Animal husbandry and mouse experiments were performed in accordance with all University of North Carolina at Chapel Hill Institutional Animal Care and Use Committee guidelines. Construction of ChikV TM Deletion Mutants.

A full-length cDNA clone of Chikungunya, West African strain 37997, in the pSinRep5 vector (Genbank #EU224270, incorporated herein by reference (SEQ ID NO:21)) was obtained (Tsetsarkin et al. 2006). Deletions in the E2 TMD of ChikV were produced by PCR based site-directed mutagenesis, using Pfu Turbo® DNA polymerase AD (Stratagene, La Jolla, Calif.). Primers designed were to create sets of 9 amino acid (aa) deletions within ChikV E2 so that the TMD size was 17 aa in length (TM17-1, 2 and 3) (Table 1). Reactions were run with and without DMSO (4% final concentration) in 1.5× buffer. PCR cycles were: 95° C., 2 min, ×25 cycles of 95° C. for 15 sec, 45 sec annealing (TA=Primer Tm −5° C. for each set of primers), 68° C. for 24 min. Extension, 28 min at 68° C.; samples were then held at 4° C. Following mutagenesis, the PCR products were digested with Dpn I (New England Biolabs) and transformed into SURE®2 Supercompetent *E. coli* cells (Stratagene) as per manufacturer's instructions with a few alterations. Following heat shock and recovery on ice, RT NZY+ broth (Teknova, Hollister, Calif.) was added and incubated at 30° C. for 2 hours. After plating on LB agar containing 50 µg/mL carbenicillin (Teknova), incubation was 30° C. for 32-48 hours. A colony PCR screen was used to identify mutations. Growth of all ChikV clones in SURE®2 cells was in LB containing 50 µg/mL carbenicillin at 28 to 30° C. for approximately 24 to 48 hours. ChikV plasmid DNA was recovered using the Wizard® Plus Minipreps (Promega, Madison, Wis.). All ChikV deletion mutant clones were confirmed by sequence analysis (Eurofins MWG Operon, Huntsville, Ala.). Purified DNA produced full-length ChikV RNAs were transcribed in vitro with SP6 RNA polymerase and transfected into C7-10 cells for stock virus production, Cell and Virus Culture BHK and C7-10 mosquito cell lines were maintained as previously described (Hernandez et al. 2010) in minimal essential medium (MEM-E) containing Earl's salts, supplemented with 10% fetal bovine serum (FBS), 5% tryptose phosphate broth, and 5 mM L-glutamine. C7-10 cells were transfected by electroporation with WT ChikV and ChikV TM17 series mutant RNAs. Supernatants were harvested 2 days post transfection and stored at −80° C. with 10% glycerol added. Infections in sub-confluent monolayers of BHK and C7-10 were performed using virus from these transfections. Virus harvested from transfections and infections in vitro was titrated by plaque assay in C7-10 cells to test for a host-range phenotype. Assays were stained 48 hours post inoculation with 1×MEM-E completed media containing 0.06% neutral red and 1% agarose. *Spodoptera*

*frugiperda* (Sf9) cells were cultured at 28° C. in Grace's medium (Gibco) completed with 10% FBS. Suspension cultures were seeded at a density of $3\times10^5$ cells per mL, and allowed to grow to a density of $2\times10^6$ cells/mL. 24 hours prior to infection, adherent flasks were seeded with cells from suspension cultures and incubated at 28° C. Subconfluent adherent Sf9 cells were infected with a multiplicity of infection (MOI) of >1 plaque forming units (pfu)/cell of ChikV or ChikV TM17-2, for 1 hr. with rocking and inoculum was removed and replaced with Grace's medium completed with 10% FBS or uncompleted Grace's medium. Supernatants were harvested after 19 hr. of incubation at 28° C. Virus was titered via plaque assay in C7-10 cells as described above. Similar studies were also completed for the ChikV TM16 series of the mutants.

Mouse Studies

Previous studies have described ChikV disease in C57BL/6J mice (Couderc et al. 2008; Morrison et al. 2011) which were also chosen for the testing of the ChikV vaccine strains. C57BL/6J mice were obtained from the Jackson Laboratory (Bar Harbor, Me.) and were injected at 14 days of age in the left hind footpad (Kamala 2007). Mice were weighed every day and no mortality occurred from ChikV infection. Swelling and inflammation were measured laterally and longitudinally along the foot below the ankle Fourteen day old mice were infected via subcutaneous injection into the left foot pad with $\sim10^3$ pfu of WT ChikV, TM17-1, TM17-2, and TM17-3, ChikV in 10 µL of completed MEM with 10% glycerol. Animals, including those from a naïve group of mice injected with media only, were sacrificed 1, 2, 3, 7, 10, and 21 days post injection (dpi) to evaluate viremia, persistence in the tissues, neutralizing antibody titer (NAb), IgG production, and tissue disease. Observations were made 1-10 days post vaccination to evaluate physical stress, swelling, or disability to the mouse foot pad due to virus infection. One of the first markers for pathology is swelling at the site of infection. WT virus produced severe swelling, TM17-3 reactogenicity was only slight while TM17-1 and TM17-2 had no measurable swelling. Because swelling is linked to other pathology only the mutants which did not produce swelling at the site of infection were challenged, eliminating TM17-3. Animals from which tissues were prepared to evaluate disease were perfused with paraformaldehyde, imbedded in paraffin and processed for H and E staining on 7, 10 and 21 dpi. Based on results from the initial evaluation of the vaccine candidates; naïve mice and mice injected with TM17-1, and TM17-2 were used to test for protection from infection with a more pathogenic strain of ChikV. Twenty eight dpi the majority of mice from each group were challenged via subcutaneous injection in the foot pad with 103 pfu WT ChikV(SL15649) (Morrison et al. 2011), while 3 mice from each vaccine group were injected with media as a control test for any residual response from the original vaccination. Mice were sacrificed 1, 2, 3, and 7 days post challenge to again evaluate viremia, tissue disease, and NAb.

Viremia from Mice

Due to the selective nature of the ChikV strain for growth in mosquitoes (Tsetsarkin et al. 2006; Delatte et al. 2010; Vazeille et al. 2007), and the attenuation of the vaccine strains in mammalian cells, vaccine titers and viremias from mice were quantified by plaque assay in C7-10 as described (Hernandez et al. 2010). Viremias resulting from the challenge virus ChikV SL15649 were quantified by plaque assay on BHK due to the selective nature of this virus for mammalian cells (personal observation and this study). The limit of detection for these assays was <40 pfu per gram of tissue (pfu/g), and the results expressed are the arithmetic means of titers obtained from 3 mice per group per day, shown in FIG. 1.

Persistence of Infection in Tissues

ChikV is known to persist in the joints of the host, producing chronic arthralgia. To determine if mutant virus persisted in the vaccinated animals, tissues and sera from infected and naïve mice 10 and 21 days post vaccination were homogenized and RNA extracted using Trizol® LS reagent and the Purelink® RNA kit (Life Technologies Inc. Grand Island, N.Y.) and suspended in water. Extracted RNAs were then analyzed via RT-PCR (reverse transcription-polymerase chain reaction) using the following primer pairs; Sense primer: CHIKV 10007F (5'-CAG TGA TCC CGA ACA CGG TG-3'; SEQ ID NO:24) Anti-sense primer: CHIKV 10260R (5'-CCA CAT AAA TGG GTA GAC TCC-3'; SEQ ID NO:25) which recognize the ChikV strain (sequences courtesy of Kristen Long, UNC Chapel Hill). The plasmid icCHIKV SL15649 was used as a positive control, and extracted RNA was used as a negative control. RT-PCR had a sensitivity of detection of ~10 pfu.

Plaque Reduction Neutralization Test

Neutralizing antibody (NAb) titers were determined by plaque reduction neutralization test (PRNT) in BHK cells (Smith et al. 2012). Mice sera were heat inactivated at 56° C. for 20 minutes prior to being serially diluted in duplicate 1 to 2, starting with a 1 to 20 dilution. After diluting the sera, approximately 20 pfu of WT ChikV were added to each dilution, allowed to incubate at RT for 15 minutes, and then plated on BHK and allowed to produce plaques for 2 days at 37° C. NAb titers (PRNT50) were determined based upon the highest serial dilutions where 50% of the pfu added were observed, and results are expressed as the geometric mean of titers from the 3 mice per group per day.

Anti-ChikV IgG ELISA 96-well Poly-D-Lysine pretreated ELISA plates (Becton Dickinson, Bedford, Mass.) were coated with >100 ng of purified WT ChikV per well at 37° C. for 1 hour, blocking with PBS-D buffer with 0.2% Tween-20, and 10% FBS at 4° C. overnight. A standard of serially diluted Anti-ChikV IgG1 (#3583, ViroStat Inc, Portland, Me.) was added to the plate, as well as 1:100 dilutions of heat inactivated mouse sera in duplicate. Serum samples obtained 21 dpi and 7 days post challenge were added for 1.5 hours at RT and removed. A 1:2000 dilution of Anti-mouse IgG horseradish peroxidase conjugated (Sigma-Aldrich #A8924). Ab was then added to the plate for another 1.5 hours at RT. ELISAs were developed using TMB substrate (Promega) for 30 minutes in the dark at RT, stopped with 1% SDS, read using a Tecan Rainbow® 96-well plate reader at an absorbance wavelength of 405 nm and reference wavelength of 0. IgG concentrations are given in mg/mL as calculated from the standard curve of control antibody, and results shown are the arithmetic mean of concentrations obtained from 6 mice per group.

Reactogenicity

The first part of the study evaluated inflammation and swelling of the foot and ankle at the site of injection of each of the viruses injected, compared to a control group. Inflammation was monitored for 10 dpi. Severity grades were assigned as minimal, mild, moderate or marked. WT ChikV infected mice displayed mild to moderate inflammation beginning 2 dpi (data not shown) while ChikV TM17-3 exhibited inflammation in the minimal category and was eliminated from the study at the challenge phase.

Histopathology

Mice were sacrificed and perfused by intracardial injection with 4% paraformaldehyde, pH 7.3 on the days indicated. Hind limb tissues were embedded in paraffin and 5 μm sections were prepared (Morrison et al. 2011). Hemotoxylin and Eosin (H and E) stain was used to determine the extent of inflammation of the tissue and tissue disease. Sections were evaluated for fasciitis in the foot/ankle and quadriceps (quad) as in (Morrison et al. 2011).

Example 2—Study Results and Discussion

Host Range Mutant Design

Figure 6:
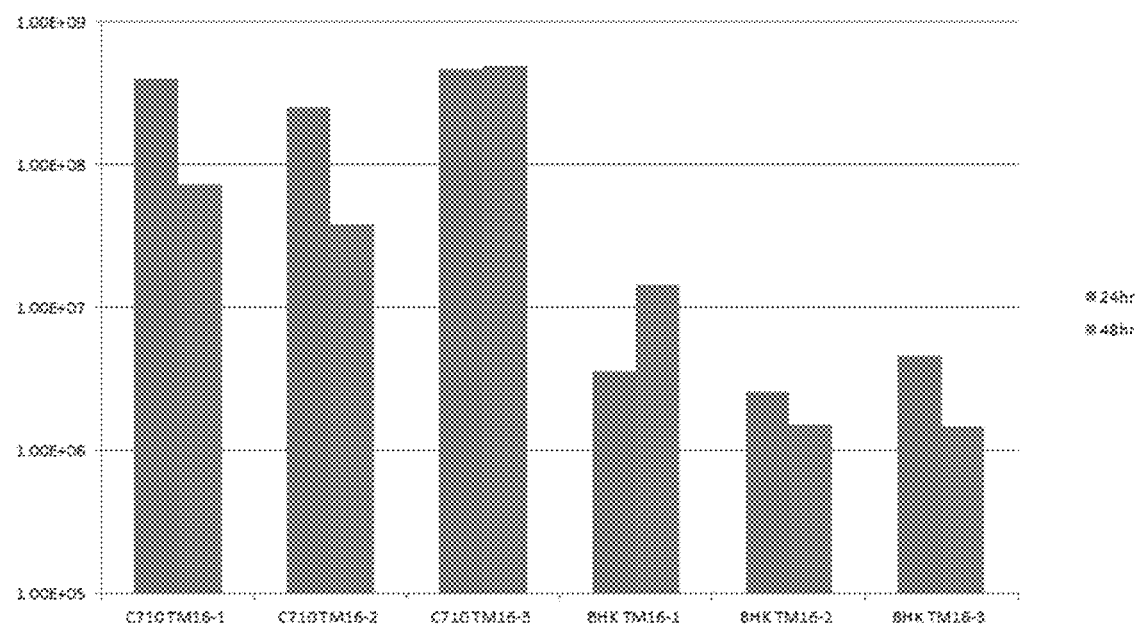
FIG. 6: Graph shows the growth of ChikV TM16 (TM16-1, TM16-2 and TM-16-3) mutants in C710 insect cells versus mammalian BHK cells. In each case viral titer is show at 24 hour and 48 hour time points (left and right bars respectively).

The 26 amino acid sequence defining the ChikV TMD was determined by comparison to the SIN TMD and the junction with the endodomain (Hernandez et al. 2000; Rice et al. 1982; Ahlquist et al. 1985; Strauss et al. 1994; Hernandez et al. 2005). Because of the specific geometry of the helical TMD and the differences in the amino acid sequence in ChikV; it was not clear which amino acid deletions might result in desired HR phenotype. A series of 3 TM17 mutants were made, deleting the sequences shown in Table 1A. TM17-3 represented the most central deletion whereas two other mutants, ChikV TM17-1 and TM17-2 were designed to shift the deleted sequence toward the amino and carboxyl termini, respectively. Likewise, a series of TM16 mutants were made, deleting the sequences shown in Table 1B. Virus titers of the ChikV mutants were determined after growth in both BHK and C7-10 cells. All ChikV TM 17 mutants had titers in the range of $10^6$ from BHK and $10^7$ from C7-10 cells (Table 1A). Similarly, ChikV TM 16 mutants had titers in the range of $10^6$ from BHK and $10^7$-$10^8$ from C7-10 cells (Table 1C and FIG. 6).

TABLE 1A

Transmembrane domain sequences of SIN (SEQ ID NO: 13) compared to ChikV37997 (SEQ ID NO: 14) are shown. Three transmembrane deletions (each deletion of 9 amino acids) of ChikV were produced in vitro and studied. The underlined portions of sequence represent the segments of the TMD which were deleted. Titers shown demonstrate the host range phenotype existing in each of these deletion mutants. TM17 designates the predicted number of amino acids remaining in the TMD in these mutants.

| Mutants | | E2 TMD Sequence | Titers pfu/mL | |
|---|---|---|---|---|
| | | | BHK | C7-10 |
| SIN | HR* | $_{365}$VYTILAVASATVAMMIGVTVAVLCAC$_{390}$ | 1 × $10^7$ | 1 × $10^9$ |
| ChikV | 37997 | $_{365}$TMTVVIVSVASFVLLSMVGTAVGMCV$_{390}$ | 3 × $10^8$ | 5 × $10^8$ |
| ChikV | TM17-1 | $_{365}$TMTVVIVSVASFVLLSMVGTAVGMCV$_{390}$ | 5 × $10^6$ | 7 × $10^7$ |
| ChikV | TM17-2 | $_{365}$TMTVVIVSVASFVLLSMVGTAVGMCV$_{390}$ | 5 × $10^6$ | 5 × $10^7$ |
| ChikV | TM17-3 | $_{365}$TMTVVIVSVASFVLLSMVGTAVGMCV$_{390}$ | 5 × $10^6$ | 2 × $10^7$ |

*HR indicates heat resistant strain.

TABLE 1B

Transmembrane domain sequences of SIN (SEQ ID NO: 13) compared to ChikV37997 (SEQ ID NO: 14) are shown. Three additional transmembrane deletions (each deletion of 10 amino acids) of ChikV were produced. The underlined portions of sequence represent the segments of the TMD which were deleted.

| Virus Strain/Mutant | E2 TMD Sequence | Deleted amino acids (base pairs) |
|---|---|---|
| SINV HR* | $_{365}$VYTILAVASATVAMMIGVTVAVLCAC$_{390}$ | none |
| CHIKV 37997 | $_{365}$TMTVVIVSVASFVLLSMVGTAVGMCV$_{390}$ | none |
| CHIKV TM16-1 | $_{365}$TMTVVIVSVASFVLLSMVGTAVGMCV$_{390}$ | 372-381 (1116-1143) |
| CHIKV TM16-2 | $_{365}$TMTVVIVSVASFVLLSMVGTAVGMCV$_{390}$ | 374-383 (1122-1149) |
| CHIKV TM16-3 | $_{365}$TMTVVIVSVASFVLLSMVGTAVGMCV$_{390}$ | 373-382 (1119-1146) |

*HR indicates heat resistant strain.

TABLE 1C

ChikV TM16 mutant viruses shown in Table 1B were grown in C7-10 mosquito cells or mammalian BHK cells and titers (in PFU) were assed at 24 and 48 hours.

| Cell line/ChikV mutant | 24 hr | 48 hr |
|---|---|---|
| C710 TM16-1 | 4.02E+08 | 7.25E+07 |
| C710 TM16-2 | 2.53E+08 | 3.83E+07 |
| C710 TM16-3 | 4.66E+08 | 4.94E+08 |
| BHK TM16-1 | 3.56E+06 | 1.44E+07 |
| BHK TM16-2 | 2.56E+06 | 1.50E+06 |
| BHK TM16-3 | 4.57E+06 | 1.48E+06 |

Safety and Immunogenicity

Chikungunya is a virus which causes arthritis and will also establish persistent infection in the joints (Suhrbier et al. 2012). For this reason, serum as well as tissues surrounding the ankle were examined. The WT La Reunion strain was used to construct the mutant viruses. The virus titers may seem high but this virus is mosquito adapted (Tsetsarkin et al. 2007; Vanlandingham et al. 2006) and was titered on mosquito C7-10 cells. BHK cells, which were not found to be good indicator cells for this ChikV strain, gave much lower titers and did not reflect the actual viremic levels. The first part of the study evaluated inflammation and swelling of the foot/ankle at the site of injection of each of the viruses injected, compared to a control group. Swelling at the site of injection is indicative of primary reactogenicity and is a good predictor of further tissue disease (Morrison et al. 2011). Both TM17-1 and TM17-2 did not produce any inflammatory response at the site of injection and proceeded to the challenge portion of the study.

Virus Viremia Post Injection.

Viremia from all virus infected mice was determined from sera and tissue samples on 1, 2, 3 and 7 dpi and are shown in FIG. 1A. All mice were injected with $10^3$ pfu/10 μL of virus each of the viruses and grew to a level of $10^7$ pfu/mL within 24 hours pi. Serum virus titers were not found to be significantly different from WT until day 2 for TM17-2 ($p<0.05$), and day 3 for TM17-1 ($p<0.001$). ChikV TM 17-1 and 2 had not cleared all virus from the serum on day 7 ($10^2$ pfu/mL). The infection profile changes when the foot/ankles are examined (FIG. 1B). Foot and ankle tissue titers differ from WT as follows; day 1 titers are significantly different from WT ($p<0.001$ for TM17-1, $p<0.01$ for TM17-2) for both TM17-1 and 2 and on day 2 only TM17-1 differs ($p<0.05$). Both TM17-1 and 2 are significantly lower than WT on day 3 ($p<0.05$ for both). By day 7 both TM17-2 and 3 are cleared from the foot/ankle ChikV titers from the quadriceps of the 3 mutants tested did not vary from WT titers on days 1 and 2 (FIG. 1C). However, for TM17-1, 2, and 3 virus was not detected on day 3 while WT virus infected animals still expressed $10^4$ pfu/g. Wild type virus is detected by RT-PCR in the serum, foot/ankle, and quad 21 days after infection indicating a persistent infection of the affected tissues and is discussed further below.

Virus Persistence in Foot/Ankle and Quad.

Virus persistence in the mice is defined by the presence of virus past 7 dpi. Persistence was evaluated by RT-PCR at days 10 and 21 post injection and is shown in Table 2. The presence of a PCR product was scored as positive or negative for each of three mice. On day 10 the ChikV infected mice tested positive for 1 mouse in the serum, 3 in the foot/ankle and 1 mouse in the quad. By day 21 this same profile was seen for a second group of 3 ChikV mice. Of the mice infected with the mutant viruses TM17-1 tested positive (1 mouse) in the foot/ankle on day 21, TM17-2 tested positive (1 mouse) from the serum on day 21, and TM17-3 tested positive (2 mice) from the serum on both days 10 and 21 post infection. The limit of detection of this assay was 10 pfu.

TABLE 2

Evaluation of persistence of ChikV RNA 10 and 21 days after injection of mice (pre-challenge) with wild type ChikV, attenuated mutants CHIKV TM-171-3, or mock (diluent) by RT-PCR. Tissues were either positive or negative for the presence of viral RNA and the number of positive symbols represents the number of mice per each sample group that tested positive (n = 3). The limit of detection for this assay was equivalent to 10 pfu.

| | 10 Days Post Injection | | | 21 Days Post Injection | | |
|---|---|---|---|---|---|---|
| Vaccine | Sera | Foot/Ankle | Quadricep | Sera | Foot/Ankle | Quadricep |
| ChikV37997 | + | +++ | + | + | +++ | + |
| TM17-1 | − | − | − | − | + | − |
| TM17-2 | − | − | − | + | − | − |
| TM17-3 | ++ | − | − | ++ | − | − |
| Naïve | − | − | − | − | − | − |

Vaccine Efficacy

To ascertain the level of vaccine efficacy animals were sacrificed 1, 2, and 3 days post challenge (28 dpi) to determine viremia and pathology. Challenge was injection with $10^3$ pfu of WT ChikV SL15649, into mice infected with TM17-1, TM17-2, WT ChikV or no vaccine (naïve). Shown in Table 3 are the viremia values measured for the indicated tissue on 3 consecutive days post challenge. It was of interest that ChikV was not more protective against challenge giving a titer of $8.5\times10^3$ pfu/g from the foot/ankle and $5.1\times102$ pfu/g from the quad on day 1. WT ChickV infected mice continued to be infected with challenge virus in the quad on day 2 ($1.3\times104$ pfu/g) which was cleared by day 3 post challenge. As is presented in Table 3, TM17-1 had a titer of $1.3\times10^4$ pfu/mL in the serum on day 1 post challenge (day 29). This is challenge virus since all pre-challenge viremia was cleared for this mutant by day 21 (refer to Table 2). ChikV TM17-1 also had a titer of $6.4\times10^2$ pfu/mL virus in the quad on day 2 post challenge. No further viremia was detected for this mutant from any tissue on day 3 post challenge in any mouse. ChikV TM17-2 had no detectable viremia in any of the tissues sampled on the 3 days post challenge. The challenge virus, ChikV SL15649 gave serum titers of $4.7\times10^7$ and $8.6\times10^5$ pfu/mL on days 1 and 2 respectively, but was cleared by day 3. ChikV SL15649 was also found to have viremia in the foot/ankle an all 3 days; $4.3\times10^3$, $7.3\times10^3$ and $9.8\times10^2$ pfu/g respectively for each day. ChikV SL15649 titers were also measured for all three days when the quad was analyzed. These values are $1.7\times10^5$, $4.0\times10^5$, and $2.1\times10^3$ pfu/g respectively on each of the 3 days post challenge. These data collectively demonstrate that ChikV infection targets the joints and surrounding musculature and that vaccination with TM17-2 protected all tissues assayed from WT virus challenge beginning day 1 of the viremic period.

TABLE 3

The titers of the viremia detected (in pfu/g) by plaque assay 1, 2, and 3 days after challenging mice with $10^3$ pfu of WT ChikV SL15649. Challenge was 28 days after injection with TM17-1, TM17-2, ChikV37997, or no vaccine (naïve). ChikV TM-3 was not challenged due to the detection of mild reactogenicity at the injection site. P values of the titers compared to the naïve virus control are given with ns designating; not statistically significant.

| | Serum | | | Foot/Ankle | | | Quadricep | | |
|---|---|---|---|---|---|---|---|---|---|
| Vaccine | Day 1 | Day 2 | Day 3 | Day 1 | Day 2 | Day 3 | Day 1 | Day 2 | Day 3 |
| TM17-1 | $1.3 \times 10^4$ | ND* | ND | ND | ND | ND | ND | $6.4 \times 10^2$ | ND |
| | $p < 0.05$ | ns | ns | $p < 0.05$ | $p < 0.001$ | $p < 0.05$ | $p < 0.01$ | $p < 0.01$ | ns |
| TM17-2 | ND | ND | ND | ND | ND | ND | ND | ND | ND |
| | $p < 0.001$ | $p < 0.001$ | ns | $p < 0.05$ | $p < 0.001$ | $p < 0.05$ | $p < 0.001$ | $p < 0.01$ | ns |
| ChikV37997 | ND | ND | ND | $8.5 \times 10^3$ | ND | ND | $5.1 \times 10^2$ | $1.3 \times 10^4$ | ND |
| | $p < 0.001$ | $p < 0.01$ | ns | $p < 0.001$ | $p < 0.001$ | $p < 0.05$ | $p < 0.001$ | $p < 0.01$ | ns |
| Naïve | $4.7 \times 10^7$ | $8.6 \times 10^5$ | ND | $4.3 \times 10^3$ | $7.3 \times 10^3$ | $9.8 \times 10^2$ | $1.7 \times 10^5$ | $4.0 \times 10^5$ | $2.1 \times 10^3$ |

*ND below detection limit of the assay, 80 pfu/mL.

Figure 4:
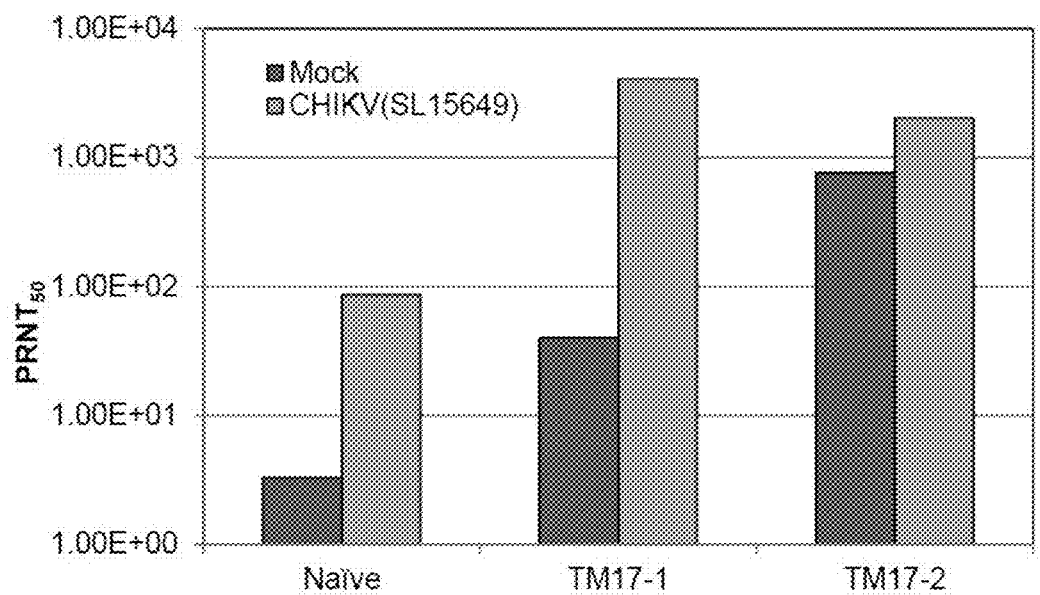
FIG. 4: Neutralizing antibody titers present in mouse sera 7 days after challenge with wild type ChikV(SL15649) or mock (diluent, complete MEM). Titers shown represent the geometric means of sera from 3 different mice per group per day.
Figure 5:
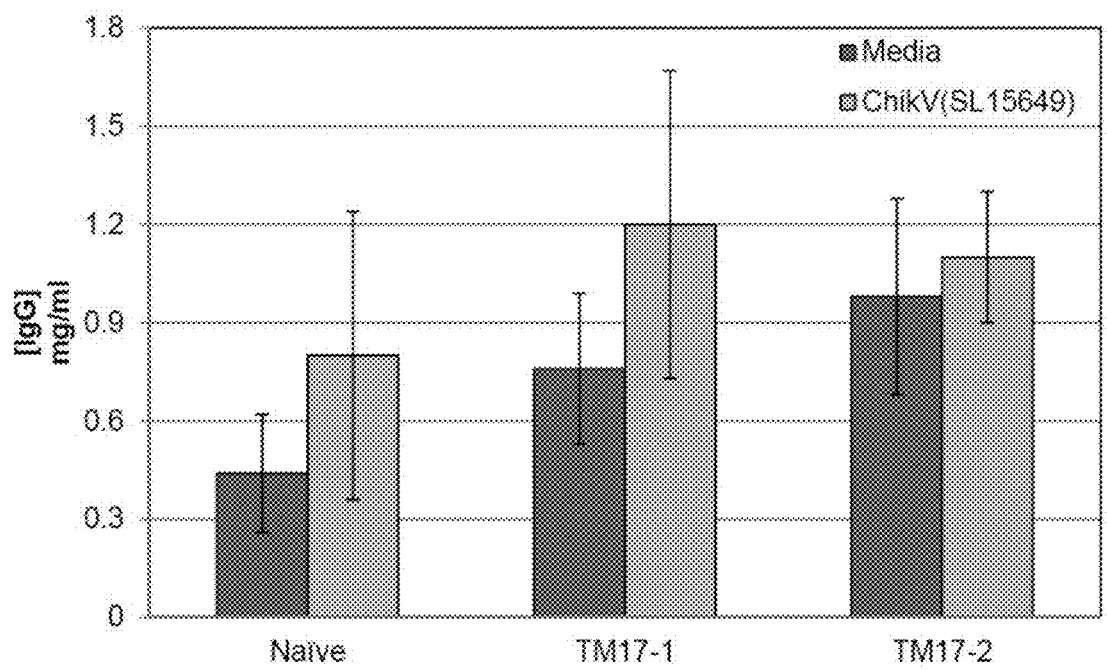
FIG. 5: Total anti-ChikV IgG concentrations (mg/mL) present in mouse serum 7 days after challenging vaccinated mice with ChikV(SL15649) or media as determined by ELISA. Error bars represent the standard deviation.

Efficacy was shown further by measuring the amount of Nab on day 7 post challenge (FIG. 4). NAb titers generated by the WT virus ChikV post inoculation were high 1000 PRNT50 on day 7, which was expected. PRNT50 titers remained high for WT ChikV and were not found to be comparable to titers of the ChikV HR mutants because of the variability of the data and the small sample size, thus all TM17 mutants appear to have similar neutralization to WT 7, 10 and 21 dpi. On day 7 post challenge. ChikV TM17-1 gave a PRNT50 titer of 4000 while TM17-2 was 2000, compared to the mock control and the amount of NAb produced by ChikV SL15649. These values are all essentially equivalent to the WT values.

Total ChikV IgG Concentration

Figure 3:
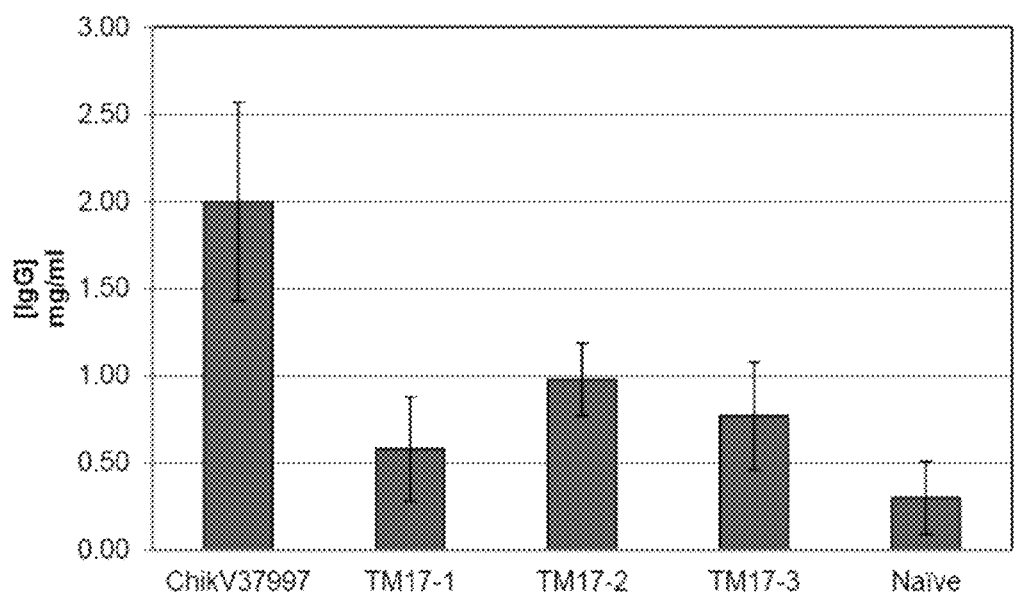
FIG. 3: Total anti-ChikV IgG concentration (mg/mL) present in mouse serum 21 days post vaccination. The amount of total WT IgG was found to be statistically higher than IgG from TM17-1, 2, and 3 (p<0.001 for Naïve, p<0.01 for TM17-1 and 3, and p<0.05 for TM17-2) while there was no significant difference found among the respective mutant pairs.

It was important to determine the total ChikV specific IgG post infection. To determine the total concentration of ChikV-specific IgG elicited by vaccination, an enzyme-linked immunosorbant assay (ELISA) was performed 21 dpi. As shown in FIG. 3, WT LAV infected animals were found to have more than 1.5 mg/mL of IgG present. Animals vaccinated with TM17-1, TM17-2, and TM17-3 had significantly lower titers of IgG, overall, compared to WT vaccinated animals. There was no significant difference in IgG titers between the vaccine candidates. All 3 TM17 mutants were found to elicit ~4 times less total ChikV specific Ab TM17-1, ($p<0.01$), TM17-2 ($p<0.05$), TM17-3 ($p<0.01$) and mock, ($p<0.001$) while there was no significant difference found between the respective mutant pairs. (WT ChikV). Thus while virus neutralization for each of these viruses was not found to significantly differ, the total amount of IgG of each of the HR mutants was significantly lower than that of the WT inoculation indicating a favorable low ratio of non-neutralizing to neutralizing antibody. Surprisingly, the levels of total IgG did not change for TM17-1 or TM17-2 whether they were challenged or remained unchallenged. Because this was an unexpected finding no additional mice were planned to evaluate cellular immune response.

Histopathology

It was important to determine if any tissue pathology presented as a result of vaccination with TM17-1 or TM17-2. To determine this, sections of mouse foot/ankle joints were taken at 7 days postvaccination, H&E stained, and scored blindly. Pathology was assessed by scoring slides from each animal based on muscle inflammation, muscle necrosis, tendonitis, synovitis, and perivasculitis. For scoring pathology, the following scale was used: 0, 0 to 2%; 1, 2 to 20%; 2, 20 to 40%; 3, 40 to 60%; 4, 60 to 80%; and 5, 80 to 100%. For scoring of synovium and perivascular inflammation, the following scale was used: 0, no change; 1, minimal; 2, mild (inflammatory infiltrate); 3, moderate; 4, severe (destruction of synovial membrane). Scores for individual animals postvaccination are shown in Table 4. Infection of mice with WT ChikV produced severe muscle inflammation and necrosis with apparent destruction of the synovial membrane. In contrast, animals vaccinated with TM17-1 displayed mild muscle inflammation with no other signs of pathology. Importantly, animals vaccinated with TM17-2 displayed no signs of any pathology at 7 days postvaccination. These results confirm the primary reactogenicity studies, in which no swelling was seen in animals vaccinated with TM17-2.

TABLE 3

Pathology scoring assigned to slides for individual animals for foot/ankle sections taken 7 days after vaccination.

| | Score | | | | |
|---|---|---|---|---|---|
| Group/ mouse | Muscle Inflammation[a] | Muscle Necrosis[a] | Tendonitis[a] | Synovitis[b] | Perivasculitis[b] |
| WT/1 | 5 | 5 | 1 | 3 | 3 |
| WT/2 | 5 | 5 | 1 | 4 | 2 |
| WT/3 | 5 | 5 | 1 | 4 | 2 |
| TM17-1/1 | 1 | 0 | 0 | 0 | 0 |
| TM17-1/2 | 0 | 0 | 0 | 0 | 0 |
| TM17-1/3 | 1 | 0 | 0 | 0 | 0 |
| TM17-2/1 | 0 | 0 | 0 | 0 | 0 |
| TM17-2/2 | 0 | 0 | 0 | 0 | 0 |
| TM17-2/3 | 0 | 0 | 0 | 0 | 0 |

[a]Scale: 0, 0 to 2%; 1, 2 to 20%; 2, 20 to 40%; 3, 40 to 60%; 4, 60 to 80%; 5, 80 to 100%.
[b]Scale: 0, no change; 1, minimal; 2, mild (inflammatory infiltrate); 3, moderate; 4, severe (destruction of synovial membrane).

To determine if vaccination with TM17-1 or TM17-2 protected animals from developing ChikV-associated pathology during challenge, foot/ankle sections of mice were taken at 7 days postchallenge, H&E stained, and scored for pathology as described above (see, Table 5). Naive mice challenged with ChikV SL15649 displayed moderate muscle inflammation and necrosis. Mice vaccinated with TM17-1 displayed minimal muscle inflammation following challenge with ChikV SL15649, with no other pathology apparent. Most importantly, samples taken from mice vaccinated with TM17-2 prior to challenge with ChikV SL15649 had no detectable pathology and appeared similar to samples taken from naive mice challenged with medium alone. Taken together, these data suggest that TM17-2 is not only nonreactogenic, it is also sufficient to protect mice from pathology associated with ChikV infection. This suggests that TM 17-2 is a ChikV vaccine strain that warrants further investigation and development as a live-attenuated vaccine strain (LAV).

TABLE 5

Pathology scoring assigned to slides for individual animals for foot/ankle sections taken 7 days postchallenge.

| Group/mouse (challenge)[a] | Score | | | | |
|---|---|---|---|---|---|
| | Muscle Inflammation[a] | Muscle Necrosis[b] | Tendonitis[b] | Synovitis[c] | Perivasculitis[c] |
| Naive/1 (mock) | 0 | 0 | 0 | 0 | 0 |
| Naive/2 (mock) | 0 | 0 | 0 | 0 | 0 |
| Naive/3 (mock) | 0 | 0 | 0 | 0 | 0 |
| Naive/1 (challenged) | 3 | 1 | 0 | 1 | 0 |
| Naive/2 (challenged) | 4 | 3 | 0 | 2 | 0 |
| Naive/3 (challenged) | 3 | 2 | 0 | 3 | 0 |
| TM17-1/1 (mock) | 0 | 0 | 0 | 0 | 0 |
| TM17-1/2 (mock) | 0 | 0 | 0 | 0 | 0 |
| TM17-1/3 (mock) | 0 | 0 | 0 | 0 | 0 |
| TM17-1/1 (challenged) | 0 | 0 | 0 | 0 | 0 |
| TM17-1/2 (challenged) | 2 | 0 | 0 | 0 | 0 |
| TM17-1/3 (challenged) | 0 | 0 | 0 | 0 | 0 |
| TM17-2/1 (mock) | 0 | 0 | 0 | 0 | 0 |
| TM17-2/2 (mock) | 0 | 0 | 0 | 0 | 0 |
| TM17-2/3 (mock) | 0 | 0 | 0 | 0 | 0 |
| TM17-2/1 (challenged) | 0 | 0 | 0 | 0 | 0 |
| TM17-2/2 (challenged) | 0 | 0 | 0 | 0 | 0 |
| TM17-2/3 (challenged) | 0 | 0 | 0 | 0 | 0 |

[a]Challenge, challenged with ChikV SL15649; mock, mock challenged.
[b]Scale: 0, 0 to 2%; 1, 2 to 20%; 2, 20 to 40%; 3, 40 to 60%; 4, 60 to 80%; 5, 80 to 100%.
[c]Scale: 0, no change; 1, minimal; 2, mild (inflammatory infiltrate); 3, moderate; 4, severe (destruction of synovial membrane).

Discussion

This study of ChikV HR mutants TM17-1, 2, and 3 can provide the basis for viral vaccine compositions. The large deletions, such as those studied, do not revert in vitro or in vivo (Smith et al. 2012). One mutant, ChikV TM17-2 did not produce any swelling at the site of injection, produced little if any inflammation in the foot/ankle or quad and did not persist in any tissue tested pre-challenge. Of the 2 HR mutants that were challenged, ChikV TM17-2 also protected against infection compared to TM 17-1 and WTChikV. Assay of the serum, foot/ankle and quad on days 1-3 post challenge did not detect any virus for mice infected with TM 17-2, while TM17-1 and LAR both allowed growth of challenge virus. Considering that infection of humans with an arbovirus confers lifelong immunity, ChikV TM17-2 protected better than infection with WTChikV which allowed a transient infection post challenge. Upon inspection of the histology, TM17-2 did not display any evidence of inflammation or tissue disease day 7 post challenge. These results suggest that ChikV TM17-2 is an attenuated, non-reactogenic, efficacious vaccine strain which should be further developed for use in humans.

Interpretation of the data suggests that the protection conferred by ChikVTM17-2 is not solely antibody-dependent. While antibodies are believed to be the primary method of protection against ChikV infection (Couderc et al. 2009), cell mediated immunity has been shown to be sufficient for protection against alphavirus disease in the absence of strong antibody response (Linn et al. 1998; Paessler et al. 2007). Although the studies here do not point directly to a specific mechanism for protection by this particular mutant there is one notable point to consider. All the ChikV TM17 mutants deleted the same number of amino acids (9) and the only distinction between these mutants is the position of the deletion with respect to the amino and carboxyl terminus of the TMD.

Upon an initial inspection of the post inoculation titers of WTChikV and TM17-1, 2 and 3, it may seem that the virus titers for WTChik and the mutants are high; however it should be considered that the mutants are mosquito adapted to the *A. albopictus* cell lines C7-10 and C6/36. These viruses were not found to plaque well on BHK and all assays were performed on C7-10 cells. The HR phenotype of these mutants has been proposed in previous studies as a marker of attenuation and now has additional support from studies in monkeys for DV2 and ChikV.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 6,306,401
U.S. Pat. No. 6,589,533
U.S. Pat. No. 7,128,915
U.S. Pat. No. 7,335,363
Ahlquist P, Strauss E G, Rice C M, Strauss J H, Haseloff J, Zimmern D. Sindbis virus proteins nsP1 and nsP2 contain homology to nonstructural proteins from several RNA plant viruses. J Virol 1985; 53(2):536-42.
Barrett A D T, Stanberry L R. Vaccines for biodefense and emerging and neglected diseases. Amsterdam; Boston: Academic, 2009.
Barrett A D, Stanberry L R, editors. Vaccines for Biodefence and Emerging and Neglected Diseases: Elsevier, 2009.
Clayton, *J. Lipid. Res.,* 15:3-19, 1964.
Coffey L L, Vasilakis N, Brault A C, Powers A M, Tripet F, Weaver S C. Arbovirus evolution in vivo is constrained by host alternation. Proceedings of the National Academy of Sciences 2008 May 13, 2008; 105(19):6970-5.
Couderc T, Chrétien F, Schilte C, Disson O, Brigitte M, Guivel-Benhassine F, et al. A Mouse Model for Chikungunya: Young Age and Inefficient Type-I Interferon Signaling Are Risk Factors for Severe Disease. PLoS Pathog 2008; 4(2):e29.
Couderc T, Khandoudi N, Grandadam M, Visse C, Gangneux N, Bagot S, et al. Prophylaxis and therapy for Chikungunya virus infection. J Infect Dis 2009; 200(4): 516-23.
Delatte H, Desvars A, Bouetard A, Bord S, Gimonneau G, Vourc'h G, et al. Blood-feeding behavior of *Aedes albopictus*, a vector of Chikungunya on La Reunion. Vector Borne Zoonotic Dis 2010 April; 10(3):249-58.

Doerfler W, Ulrich H, Bohn P. Medicine at the interface between science and ethics: Halle (Saale): Deutsche Akademie der Naturforscher Leopoldina, 2010., 2007.

Dubrulle M, Mousson L, Moutailler S, Vazeille M, Failloux A-B. Chikungunya Virus and <italic>Aedes</italic> Mosquitoes: Saliva Is Infectious as soon as Two Days after Oral Infection. PLoS One 2009; 4(6):e5895.

Dubrulle M, Mousson L, Moutailler S, Vazeille M, Failloux A-B. Chikungunya Virus and <italic>Aedes</italic> Mosquitoes: Saliva Is Infectious as soon as Two Days after Oral Infection. PLoS One 2009; 4(6):e5895.

He L, Piper A, Meilleur F, Myles D A, Hernandez R, Brown D T, et al. The structure of Sindbis virus produced from vertebrate and invertebrate hosts as determined by small-angle neutron scattering. J Virol 2010 May; 84(10):5270-6.

He L, Piper A, Meilleur F, Hernandez R, Heller W T, Brown D T. Conformational changes in Sindbis virus induced by decreased pH are revealed by small-angle neutron scattering. J Virol 2012 February; 86(4):1982-7.

Hernandez R, Lee H, Nelson C, Brown D T. A single deletion in the membrane-proximal region of the Sindbis virus glycoprotein E2 endodomain blocks virus assembly. J Virol 2000; 74(9):4220-8.

Hernandez R, Sinodis C, Horton M, Ferreira D, Yang C, Brown D T. Deletions in the transmembrane domain of a sindbis virus glycoprotein alter virus infectivity, stability, and host range. J Virol 2003 December; 77(23):12710-9.

Hernandez R, Ferreira D, Sinodis C, Litton K, Brown D T. Single amino acid insertions at the junction of the sindbis virus E2 transmembrane domain and endodomain disrupt virus envelopment and alter infectivity. J Virol 2005 June; 79(12):7682-97.

Hernandez R, Sinodis C, Brown D T. Sindbis virus: propagation, quantification, and storage. Curr Protoc Microbiol 2010 February; Chapter 15:Unit 15B 1.

Johnson D F, Druce J D, Chapman S, Swaminathan A, Wolf J, Richards J S, et al. Chikungunya virus infection in travellers to Australia. Med J Aust 2008 Jan. 7; 188(1):41-3.

Jozan M. Of Arboviruses, Arthropods, and Arthropod Cell Cultures: History and Expectations. Boca Raton, Fla.: CRC Press, 1987.

Kamala T. Hock immunization: a humane alternative to mouse footpad injections. J Immunol Methods 2007 Dec. 1; 328(1-2):204-14.

Khan A H, Morita K, Parquet Md Mdel C, Hasebe F, Mathenge E G, Igarashi A. Complete nucleotide sequence of chikungunya virus and evidence for an internal polyadenylation site. J Gen Virol 2002 December; 83(Pt 12):3075-84.

Klaassen In: Goodman and Gilman's: *The Pharmacological Basis of Therapeutics*, $8^{th}$ Ed. (1990)

Kyte & Doolittle, 1982

Labadie K, Larcher T, Joubert C, Mannioui A, Delache B, Brochard P, et al. Chikungunya disease in nonhuman primates involves long-term viral persistence in macrophages. The Journal of Clinical Investigation 2010; 120(3):894-906.

Lakshmi V, Neeraja M, Subbalaxmi M V S, Parida M M, Dash P K, Santhosh S R, et al. Clinical Features and Molecular Diagnosis of Chikungunya Fever from South India. Clinical Infectious Diseases 2008 May 1, 2008; 46(9):1436-42.

Linn M L, Mateo L, Gardner J, Suhrbier A. Alphavirus-specific cytotoxic T lymphocytes recognize a cross-reactive epitope from the capsid protein and can eliminate virus from persistently infected macrophages. Journal of Virology 1998; 72(6):5146-53.

Mak C. Drug pipeline: 1Q12. Nat Biotech 2012; 30(5):383-.

Mavalankar D, Shastri P, Bandyopadhyay T, Parmar J, Ramani K V. Increased mortality rate associated with chikungunya epidemic, Ahmedabad, India. Emerg Infect Dis 2008 March; 14(3):412-5.

McKnight K L, Simpson D A, Lin S C, Knott T A, Polo J M, Pence D F, et al. Deduced consensus sequence of Sindbis virus strain AR339: mutations contained in laboratory strains which affect cell culture and in vivo phenotypes. Journal of Virology 1996; 70(3):1981-9.

Mitsuhashi et al., *Cell Biol. Int. Rep.,* 7(12):1057-62, 1983.

Morrison T E, Oko L, Montgomery S A, Whitmore A C, Lotstein A R, Gunn B M, et al. A mouse model of chikungunya virus-induced musculoskeletal inflammatory disease: evidence of arthritis, tenosynovitis, myositis, and persistence. Am J Pathol 2011 January; 178(1):32-40.

Paessler S, Yun N E, Judy B M, Dziuba N, Zacks M A, Grund A H, et al. Alpha-beta T cells provide protection against lethal encephalitis in the murine model of VEEV infection. Virology 2007; 367(2):307-23.

Paul B J, Pannarkady G, Moni S P, Thachil E J. Clinical profile and long-term sequelae of Chikungunya fever. Indian Journal of Rheumatology 2011; 6(1, Supplement): 12-9.

Pialoux G, Gauzere B A, Jaureguiberry S, Strobel M. Chikungunya, an epidemic arbovirosis. Lancet Infect Dis 2007 May; 7(5):319-27.

Piper A, Ribeiro M, Smith K M, Briggs C M, Huitt E, Nanda K, Spears C J, Quiles M, Cullen J, Thomas M E, Brown D T, Hernandez R., *J. Virol.* 2013 June; 87(12):6748-57, 2013.

Powers A M, Brault A C, Tesh R B, Weaver S C. Re-emergence of chikungunya and o'nyong-nyong viruses: evidence for distinct geographical lineages and distant evolutionary relationships. Journal of General Virology 2000 Feb. 1, 2000; 81(2):471-9.

Ramful D, Carbonnier M, Pasquet M, Bouhmani B, Ghazouani J, Noormahomed T, et al. Mother-to-Child Transmission of Chikungunya Virus Infection. The Pediatric Infectious Disease Journal 2007; 26(9):811-5 10.1097/INF.0b013e3180616d4f.

Remington's Pharmaceutical Sciences, 18th Ed. Mack Printing Company, 1990.

Rezza G, Nicoletti L, Angelini R, Romi R, Finarelli A C, Panning M, et al. Infection with chikungunya virus in Italy: an outbreak in a temperate region. The Lancet. 2007 Dec. 1; 370(9602):1840-6.

Rice C M, Bell J R, Hunkapiller M W, Strauss E G, Strauss J H. Isolation and characterization of the hydrophobic COOH-terminal domains of the sindbis virion glycoproteins. J Mol Biol 1982 Jan. 15; 154(2):355-78.

Rogers K M, Heise M. Modulation of cellular tropism and innate antiviral response by viral glycans. J Innate Immun 2009; 1(5):405-12.

Sambrook et al., In: *Molecular Cloning: a Laboratory Manual,* $2^{nd}$ Ed., Cold Spring Harbor Laboratory Press, Cold Spring Harbor, N.Y., 1987.

Shabman R S, Morrison T E, Moore C, White L, Suthar M S, Hueston L, et al. Differential induction of type I interferon responses in myeloid dendritic cells by mosquito and mammalian-cell-derived alphaviruses. J Virol 2007; 81(1):237-47.

Smith K M, Nanda K, Spears C J, Ribeiro M, Vancini R, Piper A, et al. Structural mutants of dengue virus 2 transmembrane domains exhibit host-range phenotype. Virol J 2011; 8:289.

Smith K M, Nanda K, Spears C J, Piper A, Ribeiro M, Quiles M, et al. Testing of Novel Dengue Virus 2 Vaccines in African Green Monkeys: Safety, Immunogenicity, and Efficacy. The American Journal of Tropical Medicine and Hygiene 2012 Aug. 13, 2012.

Strauss J H, Strauss E G. The Alphaviruses: Gene Expression, Replication, and Evolution. Micro. Rev. 58:491-562. Micro Rev 1994; 58:491-562.

Suhrbier A, Jaffar-Bandjee M C, Gasque P. Arthritogenic alphaviruses—an overview. Nat Rev Rheumatol 2012 July; 8(7):420-9.

Tsetsarkin K, Higgs S, McGee C E, De Lamballerie X, Charrel R N, Vanlandingham D L. Infectious clones of Chikungunya virus (La Reunion isolate) for vector competence studies. Vector Borne Zoonotic Dis 2006 Winter; 6(4):325-37.

Tsetsarkin K A, Vanlandingham D L, McGee C E, Higgs S. A single mutation in chikungunya virus affects vector specificity and epidemic potential. PLoS Pathog 2007 December; 3(12):e201.

Vanlandingham D L, Tsetsarkin K, Klingler K A, Hong C, McElroy K L, Lehane M J, et al. Determinants of vector specificity of o'nyong nyong and chikungunya viruses in *Anopheles* and *Aedes* mosquitoes. Am J Trop Med Hyg 2006 April; 74(4):663-9.

Vazeille M, Moutailler S, Coudrier D, Rousseaux C, Khun H, Huerre M, et al. Two Chikungunya isolates from the outbreak of La Reunion (Indian Ocean) exhibit different patterns of infection in the mosquito, *Aedes albopictus*. PLoS One 2007; 2(11):e1168.

WHO. Weekly epidemiological record. 2007; 2007, 82, 409-416 No. 47

Zhang et al., Susceptibility of the Sf9 insect cell line to infection with adventitious viruses. *Biologicals*, 22(3): 205-13, 1994.

---

What is claimed is:

1. A recombinant polypeptide wherein the polypeptide comprises an amino acid sequence at least 94% identical to SEQ ID NO:1 and comprises a deletion of 9-11 amino acids in the transmembrane domain (TMD) corresponding to amino acid positions 372-380, 374-382 or 373-381 of SEQ ID NO:1.

2. The polypeptide of claim 1, wherein the polypeptide is at least 95% or 96% identical to SEQ ID NO:1.

3. The polypeptide of claim 1, wherein the polypeptide comprises a deletion of 9 amino acids in the TMD.

4. The polypeptide of claim 1, wherein the polypeptide comprises SEQ ID NO:3; SEQ ID NO:5 or SEQ ID NO:7.

5. The polypeptide of claim 1, wherein the polypeptide comprises a deletion of 10 amino acids in the TMD.

6. The polypeptide of claim 5, wherein the polypeptide comprises a deletion of the amino acids corresponding to amino acid positions 372-381 of SEQ ID NO:1.

7. The polypeptide of claim 5, wherein the polypeptide comprises a deletion of the amino acids corresponding to amino acid positions 374-383 of SEQ ID NO:1.

8. The polypeptide of claim 5, wherein the polypeptide comprises a deletion of the amino acids corresponding to amino acid positions 373-382 of SEQ ID NO:1.

9. The polypeptide of claim 1, wherein the polypeptide comprises SEQ ID NO:15; SEQ ID NO:17 or SEQ ID NO:19.

10. A polynucleotide molecule encoding a polypeptide of claim 1.

11. The polynucleotide of claim 10, comprising a sequence at least 90% identical to SEQ ID NO:2.

12. The polynucleotide of claim 11, comprising a sequence of SEQ ID NO:4; SEQ ID NO:6; SEQ ID NO:8; SEQ ID NO:16; SEQ ID NO:18; or SEQ ID NO:20.

13. An isolated host cell comprising the polynucleotide of claim 10.

14. The isolated cell of claim 13, wherein the isolated cell is an insect cell.

15. The isolated cell of claim 14, wherein the isolated insect cell is a SF9 cell.

* * * * *

SEQUENCE LISTING

```
<160> NUMBER OF SEQ ID NOS: 25

<210> SEQ ID NO 1
<211> LENGTH: 423
<212> TYPE: PRT
<213> ORGANISM: Chikungunya virus

<400> SEQUENCE: 1

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Ile Asp Gln
    210                 215                 220
```

```
Cys His Ala Ala Val Thr Asn His Lys Asn Trp Gln Tyr Asn Ser Pro
225                 230                 235                 240

Leu Val Pro Arg Asn Ala Glu Leu Gly Asp Arg Lys Gly Lys Ile His
            245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Thr Met Leu Leu Tyr
            275                 280                 285

Pro Asp His Pro Thr Leu Leu Ser Tyr Arg Asn Met Gly Gln Glu Pro
            290                 295                 300

Asn Tyr His Glu Glu Trp Val Thr His Lys Lys Glu Val Thr Leu Thr
305                 310                 315                 320

Val Pro Thr Glu Gly Leu Glu Val Thr Trp Gly Asn Asn Glu Pro Tyr
            325                 330                 335

Lys Tyr Trp Pro Gln Met Ser Thr Asn Gly Thr Ala His Gly His Pro
            340                 345                 350

His Glu Ile Ile Leu Tyr Tyr Tyr Glu Leu Tyr Pro Thr Met Thr Val
            355                 360                 365

Val Ile Val Ser Val Ala Ser Phe Val Leu Leu Ser Met Val Gly Thr
370                 375                 380

Ala Val Gly Met Cys Val Cys Ala Arg Arg Arg Cys Ile Thr Pro Tyr
385                 390                 395                 400

Glu Leu Thr Pro Gly Ala Thr Val Pro Phe Leu Leu Ser Leu Leu Cys
            405                 410                 415

Cys Val Arg Thr Thr Lys Ala
            420

<210> SEQ ID NO 2
<211> LENGTH: 1269
<212> TYPE: DNA
<213> ORGANISM: Chikungunya virus

<400> SEQUENCE: 2
agtactaagg acaattttaa tgtctataaa gccacaagac catatctagc tcattgtcct      60
gactgcggag aagggcattc gtgccacagc cctatcgcat tggagcgcat cagaaatgaa     120 gcaacgacg gaacgctgaa atccaggtc tctttgcaga tcgggataaa gacagatgac      180
agccacgatt ggaccaagct gcgctatatg gatagccata cgccagcgga cgcggagcga     240
gccggattgc ttgtaaggac ttcagcaccg tgcacgatca ccgggaccat gggacacttt     300
attctcgccc gatgcccgaa aggagagacg ctgacagtgg gatttacgga cagcagaaag     360
atcagccaca catgcacaca cccgttccat catgaaccac tgtgataggt agggagagg     420 ttccactctc gaccacaaca tggtaaagag ttaccttgca gcacgtacgt gcagagcacc     480
gctgccactg ctgaggagat agaggtgcat atgcccccag atactcctga ccgcacgctg     540
atgacgcagc agtctggcaa cgtgaagatc acagttaatg gcagacggt gcggtacaag     600 tgcaactgcg gtggctcaaa cgagggactg acaaccacag acaaagtgat caataactgc     660
aaaattgatc agtgccatgc tgcagtcact aatcacaaga attggcaata caactccccct     720 ttagtcccgc gcaacgctga actcggggac cgtaaaggaa agatccacat cccattccca     780
ttggcaaacg tgacttgcag agtgccaaaa gcaagaaacc ctacagtaac ttacggaaaa     840
aaccaagtca ccatgctgct gtatcctgac catccgacac tcttgtctta ccgtaacatg     900
ggacaggaac caaattaccg cgaggagtgg gtgacacaca agaaggaggt taccttgacc     960
```

```
gtgcctactg agggtctgga ggtcacttgg ggcaacaacg aaccatacaa gtactggccg   1020
cagatgtcta cgaacggtac tgctcatggt cacccacatg agataatctt gtactattat   1080
gagctgtacc ccactatgac tgtagtcatt gtgtcggtgg cctcgttcgt gcttctgtcg   1140
atggtgggca cagcagtggg aatgtgtgtg tgcgcacggc gcagatgcat tacaccatat   1200
gaattaacac caggagccac tgttcccttc ctgctcagcc tgctatgctg cgtcagaacg   1260
accaaggcg                                                            1269
```

<210> SEQ ID NO 3
<211> LENGTH: 414
<212> TYPE: PRT
<213> ORGANISM: Artificial Sequence
<220> FEATURE:
<223> OTHER INFORMATION: recombinant polypeptide

<400> SEQUENCE: 3

```
Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser Thr His Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Ser Asn Glu
        195                 200                 205

Gly Leu Thr Thr Thr Asp Lys Val Ile Asn Asn Cys Lys Ile Asp Gln
    210                 215                 220

Cys His Ala Ala Val Thr Asn His Lys Asn Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Thr Met Leu Leu Tyr
        275                 280                 285

Pro Asp His Pro Thr Leu Leu Ser Tyr Arg Asn Met Gly Gln Glu Pro
    290                 295                 300
```

Asn Tyr His Glu Glu Trp Val Thr His Lys Lys Glu Val Thr Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Met Ser Thr Asn Gly Thr Ala His Gly His Pro
            340                 345                 350

His Glu Ile Ile Leu Tyr Tyr Tyr Glu Leu Tyr Pro Thr Met Thr Val
        355                 360                 365

Val Ile Val Met Val Gly Thr Ala Val Gly Met Cys Val Cys Ala Arg
    370                 375                 380

Arg Arg Cys Ile Thr Pro Tyr Glu Leu Thr Pro Gly Ala Thr Val Pro
385                 390                 395                 400

Phe Leu Leu Ser Leu Leu Cys Cys Val Arg Thr Thr Lys Ala
                405                 410

<210> SEQ ID NO 4
<211> LENGTH: 1242
<212> TYPE: DNA
<213> ORGANISM: Artificial Sequence
<220> FEATURE:
<223> OTHER INFORMATION: recombinant polynucleotide

<400> SEQUENCE: 4
agtactaagg acaattttaa tgtctataaa gccacaagac catatctagc tcattgtcct     60
gactgcggag aagggcattc gtgccacagc cctatcgcat tggagcgcat cagaaatgaa    120
gcaacgacg gaacgctgaa atccaggtc tctttgcaga tcgggataaa gacagatgac      180
agccacgatt ggaccaagct gcgctatatg gatagccata cgccagcgga cgcggagcga    240
gccggattgc ttgtaaggac ttcagcaccg tgcacgatca ccgggaccat gggacacttt    300
attctcgccc gatgccgaa aggagagacg ctgacagtgg gatttacgga cagcagaaag     360
atcagccaca catgcacaca cccgttccat catgaaccac ctgtgatagg tagggagagg    420
ttccactctc gaccacaaca tggtaaagag ttaccttgca gcacgtacgt gcagagcacc    480
gctgccactg ctgaggagat agaggtgcat atgcccccag atactcctga ccgcacgctg    540
atgacgcagc agtctggcaa cgtgaagatc acagttaatg gcagacggt gcggtacaag     600
tgcaactgcg gtggctcaaa cgagggactg acaaccacag acaaagtgat caataactgc    660
aaaattgatc agtgccatgc tgcagtcact aatcacaaga attggcaata caactccct     720
ttagtcccgc gcaacgctga actcggggac cgtaaaggaa agatccacat cccattccca    780
ttggcaaacg tgacttgcag agtgccaaaa gcaagaaacc ctacagtaac ttacggaaaa    840
aaccaagtca ccatgctgct gtatcctgac catccgacac tcttgtctta ccgtaacatg    900
ggacaggaac caaattacca cgaggagtgg gtgacacaca gaaggaggt taccttgacc     960
gtgcctactg agggtctgga ggtcacttgg ggcaacaacg aaccatacaa gtactggccg   1020
cagatgtcta cgaacggtac tgctcatggt caccccacatg agataatctt gtactattat  1080
gagctgtacc ccactatgac tgtagtcatt gtgatggtgg gcacagcagt gggaatgtgt   1140
gtgtgcgcac ggcgcagatg cattacacca tatgaattaa caccaggagc cactgttccc   1200
ttcctgctca gcctgctatg ctgcgtcaga acgaccaagg cg                      1242

<210> SEQ ID NO 5
<211> LENGTH: 414
<212> TYPE: PRT
<213> ORGANISM: Artificial Sequence
<220> FEATURE:

<223> OTHER INFORMATION: recombinant polypeptide

<400> SEQUENCE: 5

```
Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Ile Asp Gln
    210                 215                 220

Cys His Ala Ala Val Thr Asn His Lys Asn Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Thr Met Leu Leu Tyr
        275                 280                 285

Pro Asp His Pro Thr Leu Leu Ser Tyr Arg Asn Met Gly Gln Glu Pro
    290                 295                 300

Asn Tyr His Glu Glu Trp Val Thr His Lys Lys Glu Val Thr Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Met Ser Thr Asn Gly Thr Ala His Gly His Pro
            340                 345                 350

His Glu Ile Ile Leu Tyr Tyr Tyr Glu Leu Tyr Pro Thr Met Thr Val
        355                 360                 365

Val Ile Val Ser Val Gly Thr Ala Val Gly Met Cys Val Cys Ala Arg
    370                 375                 380

Arg Arg Cys Ile Thr Pro Tyr Glu Leu Thr Pro Gly Ala Thr Val Pro
385                 390                 395                 400
```

```
Phe Leu Leu Ser Leu Leu Cys Cys Val Arg Thr Thr Lys Ala
            405                 410
```

<210> SEQ ID NO 6
<211> LENGTH: 1242
<212> TYPE: DNA
<213> ORGANISM: Artificial Sequence
<220> FEATURE:
<223> OTHER INFORMATION: recombinant polynucleotide

<400> SEQUENCE: 6

```
agtactaagg acaattttaa tgtctataaa gccacaagac catatctagc tcattgtcct      60
gactgcggag aagggcattc gtgccacagc cctatcgcat ggagcgcat cagaaatgaa     120
gcaacggacg gaacgctgaa atccaggtc tctttgcaga tcgggataaa gacagatgac    180
agccacgatt ggaccaagct gcgctatatg gatagccata cgccagcgga cgcggagcga   240
gccggattgc ttgtaaggac ttcagcaccg tgcacgatca ccgggaccat gggacacttt   300
attctcgccc gatgcccgaa aggagagacg ctgacagtgg gatttacgga cagcagaaag   360
atcagccaca catgcacaca cccgttccat catgaaccac ctgtgatagg tagggagagg   420
ttccactctc gaccacaaca tggtaaagag ttaccttgca gcacgtacgt gcagagcacc   480
gctgccactg ctgaggagat agaggtgcat atgcccccag atactcctga ccgcacgctg   540
atgacgcagc agtctggcaa cgtgaagatc acagttaatg gcagacggt gcggtacaag    600
tgcaactgcg gtggctcaaa cgagggactg acaaccacag acaaagtgat caataactgc   660
aaaattgatc agtgccatgc tgcagtcact aatcacaaga attggcaata caactccct    720
ttagtcccgc gcaacgctga actcggggac cgtaaaggaa agatccacat cccattccca   780
ttggcaaacg tgacttgcag agtgccaaaa gcaagaaacc ctacagtaac ttacggaaaa   840
aaccaagtca ccatgctgct gtatcctgac catccgacac tcttgtctta ccgtaacatg   900
ggacaggaac caaattacca cgaggagtgg gtgacacaca gaaggaggt taccttgacc    960
gtgcctactg agggtctgga ggtcacttgg ggcaacaacg aaccatacaa gtactggccg  1020
cagatgtcta cgaacggtac tgctcatggt cacccacatg agataatctt gtactattat  1080
gagctgtacc ccactatgac tgtagtcatt gtgtcggtgg gcacagcagt gggaatgtgt  1140
gtgtgcgcac ggcgcagatg cattacacca tatgaattaa caccaggagc cactgttccc  1200
ttcctgctca gcctgctatg ctgcgtcaga acgaccaagg cg                     1242
```

<210> SEQ ID NO 7
<211> LENGTH: 414
<212> TYPE: PRT
<213> ORGANISM: Artificial Sequence
<220> FEATURE:
<223> OTHER INFORMATION: recombinant polypeptide

<400> SEQUENCE: 7

```
Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Asp Ser His Asp Trp
    50                  55                  60

Thr Lys Leu Arg Tyr Met Asp Ser His Thr Pro Ala Asp Ala Glu Arg
65                  70                  75                  80
```

Ala Gly Leu Leu Val Arg Thr Ser Ala Pro Cys Thr Ile Thr Gly Thr
            85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
            115                 120                 125

Phe His His Glu Pro Pro Val Ile Gly Arg Glu Arg Phe His Ser Arg
        130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
            165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Asn Glu
            195                 200                 205

Gly Leu Thr Thr Thr Asp Lys Val Ile Asn Asn Cys Lys Ile Asp Gln
        210                 215                 220

Cys His Ala Ala Val Thr Asn His Lys Asn Trp Gln Tyr Asn Ser Pro
225                 230                 235                 240

Leu Val Pro Arg Asn Ala Glu Leu Gly Asp Arg Lys Gly Lys Ile His
            245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Thr Met Leu Leu Tyr
            275                 280                 285

Pro Asp His Pro Thr Leu Leu Ser Tyr Arg Asn Met Gly Gln Glu Pro
        290                 295                 300

Asn Tyr His Glu Glu Trp Val Thr His Lys Lys Glu Val Thr Leu Thr
305                 310                 315                 320

Val Pro Thr Glu Gly Leu Glu Val Thr Trp Gly Asn Asn Glu Pro Tyr
            325                 330                 335

Lys Tyr Trp Pro Gln Met Ser Thr Asn Gly Thr Ala His Gly His Pro
            340                 345                 350

His Glu Ile Ile Leu Tyr Tyr Tyr Glu Leu Tyr Pro Thr Met Thr Val
            355                 360                 365

Val Ile Val Ser Val Gly Thr Ala Val Gly Met Cys Val Cys Ala Arg
        370                 375                 380

Arg Arg Cys Ile Thr Pro Tyr Glu Leu Thr Pro Gly Ala Thr Val Pro
385                 390                 395                 400

Phe Leu Leu Ser Leu Leu Cys Cys Val Arg Thr Thr Lys Ala
            405                 410

<210> SEQ ID NO 8
<211> LENGTH: 1242
<212> TYPE: DNA
<213> ORGANISM: Artificial Sequence
<220> FEATURE:
<223> OTHER INFORMATION: recombinant polynucleotide

<400> SEQUENCE: 8
agtactaagg acaattttaa tgtctataaa gccacaagac catatctagc tcattgtcct     60
gactgcggag aagggcattc gtgccacagc cctatcgcat tggagcgcat cagaaatgaa    120
gcaacggacg gaacgctgaa aatccaggtc tctttgcaga tcgggataaa gacagatgac    180

-continued

```
agccacgatt ggaccaagct gcgctatatg gatagccata cgccagcgga cgcggagcga      240
gccggattgc ttgtaaggac ttcagcaccg tgcacgatca ccgggaccat gggacacttt      300
attctcgccc gatgcccgaa aggagagacg ctgacagtgg gatttacgga cagcagaaag      360
atcagccaca catgcacaca cccgttccat catgaaccac ctgtgatagg tagggagagg      420
ttccactctc gaccacaaca tggtaaagag ttaccttgca gcacgtacgt gcagagcacc      480
gctgccactg ctgaggagat agaggtgcat atgcccccag atactcctga ccgcacgctg      540
atgacgcagc agtctggcaa cgtgaagatc acagttaatg ggcagacggt gcggtacaag      600
tgcaactgcg gtggctcaaa cgagggactg acaaccacac acaaagtgat caataactgc      660
aaaattgatc agtgccatgc tgcagtcact aatcacaaga attggcaata caactcccct      720
ttagtcccgc gcaacgctga actcgggac cgtaaaggaa agatccacat cccattccca      780
ttggcaaacg tgacttgcag agtgccaaaa gcaagaaacc ctacagtaac ttacggaaaa      840
aaccaagtca ccatgctgct gtatcctgac catccgacac tcttgtctta ccgtaacatg      900
ggacaggaac caaattacca cgaggagtgg gtgacacaca agaaggaggt taccttgacc      960
gtgcctactg agggtctgga ggtcacttgg ggcaacaacg aaccatacaa gtactggccg     1020
cagatgtcta cgaacggtac tgctcatggt cacccacatg agataatctt gtactattat     1080
gagctgtacc ccactatgac tgtagtcatt gtgtcggtgg cacagcagt gggaatgtgt     1140 gtgtgcgcac ggcgcagatg cattacacca tatgaattaa caccaggagc cactgttccc     1200
ttcctgctca gcctgctatg ctgcgtcaga acgaccaagg cg                         1242
```

<210> SEQ ID NO 9
<211> LENGTH: 423
<212> TYPE: PRT
<213> ORGANISM: Chikungunya virus

<400> SEQUENCE: 9

```
Ser Thr Lys Asp Asn Phe Asn Val Tyr Lys Ala Thr Arg Pro Tyr Leu
  1               5                  10                  15

Ala His Cys Pro Asp Cys Gly Glu Gly His Ser Cys His Ser Pro Val
             20                  25                  30

Ala Leu Glu Arg Ile Arg Asn Glu Ala Thr Asp Gly Thr Leu Lys Ile
         35                  40                  45

Gln Val Ser Leu Gln Ile Gly Ile Lys Thr Asp Asp Ser His Asp Trp
     50                  55                  60

Thr Lys Leu Arg Tyr Met Asp Asn His Met Pro Ala Asp Ala Glu Arg
 65                  70                  75                  80

Ala Gly Leu Phe Val Arg Thr Ser Ala Pro Cys Thr Ile Thr Gly Thr
                 85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
    130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp Arg Thr Leu Met Ser Gln Gln Ser Gly Asn Val Lys Ile Thr Val
```

```
                180             185             190
Asn Gly Gln Thr Val Arg Tyr Lys Cys Asn Cys Gly Gly Ser Asn Glu
            195                 200                 205
Gly Gln Thr Thr Thr Asp Lys Val Ile Asn Cys Lys Val Asp Gln
        210                 215                 220
Cys His Ala Ala Val Thr Asn His Lys Lys Trp Gln Tyr Asn Ser Pro
225                 230                 235                 240
Leu Val Pro Arg Asn Ala Glu Leu Gly Asp Arg Lys Gly Lys Ile His
            245                 250                 255
Ile Pro Phe Pro Leu Ala Asn Val Thr Cys Arg Val Pro Lys Ala Arg
        260                 265                 270
Asn Pro Thr Val Thr Tyr Gly Lys Asn Gln Val Ile Met Leu Leu Tyr
            275                 280                 285
Pro Asp His Pro Thr Leu Leu Ser Tyr Arg Asn Met Gly Glu Glu Pro
        290                 295                 300
Asn Tyr Gln Glu Glu Trp Val Met His Lys Lys Glu Val Val Leu Thr
305                 310                 315                 320
Val Pro Thr Glu Gly Leu Glu Val Thr Trp Gly Asn Asn Glu Pro Tyr
            325                 330                 335
Lys Tyr Trp Pro Gln Leu Ser Thr Asn Gly Thr Ala His Gly His Pro
        340                 345                 350
His Glu Ile Ile Leu Tyr Tyr Tyr Glu Leu Tyr Pro Thr Met Thr Val
        355                 360                 365
Val Val Val Ser Val Ala Thr Phe Ile Leu Leu Ser Met Val Gly Met
        370                 375                 380
Ala Ala Gly Met Cys Met Cys Ala Arg Arg Arg Cys Ile Thr Pro Tyr
385                 390                 395                 400
Glu Leu Thr Pro Gly Ala Thr Val Pro Phe Leu Leu Ser Leu Ile Cys
            405                 410                 415
Cys Ile Arg Thr Ala Lys Ala
            420

<210> SEQ ID NO 10
<211> LENGTH: 1269
<212> TYPE: DNA
<213> ORGANISM: Chikungunya virus

<400> SEQUENCE: 10
agcaccaagg acaacttcaa tgtctataaa gccacaagac catacttagc tcactgtccc      60
gactgtggag aagggcactc gtgccatagt cccgtagcac tagaacgcat cagaaatgaa     120
gcgacagacg gacgctgaa aatccaggtc tccttgcaaa tcggaataaa gacggatgac     180
agccacgatt ggaccaagct gcgttatatg acaaccaca tgccagcaga cgcagagagg     240
gcggggctat ttgtaagaac atcagcaccg tgtacgatta ctggaacaat gggacacttc     300
atcctggccc gatgtccaaa agggaaaact ctgacggtgg gattcactga cagtaggaag     360
attagtcatt catgtacgca cccatttcac cacgaccctc ctgtgatagg tcgggaaaaa     420
ttccattccc gaccgcagca cggtaaagag ctaccttgca gcacgtacgt gcagagcacc     480
gccgcaacta ccgaggagat agaggtacac atgcccccag acacccctga tcgcacatta     540
atgtcacaac agtccggcaa cgtaaagatc acggtcaatg ccagacggt gcggtacaag     600
tgtaattgcg gtggctcaaa tgaaggacaa acaactacag acaaagtgat taataactgc     660
aaggttgatc aatgtcatgc cgcggtcacc aatcacaaaa agtggcagta taactcccct     720
```

```
ctggtcccgc gtaatgctga acttggggac cgaaaaggaa aaattcacat cccgtttccg    780
ctggcaaatg taacatgcag ggtgcctaaa gcaaggaacc ccaccgtgac gtacgggaaa    840
aaccaagtca tcatgctact gtatcctgac cacccaacac tcctgtccta ccggaatatg    900
ggagaagaac caaactatca agaagagtgg gtgatgcata agaaggaagt cgtgctaacc    960
gtgccgactg aagggctcga ggtcacgtgg ggcaacaacg agccgtataa gtattggccg   1020
cagttatcta caaacggtac agcccatggc caccgcatg agataattct gtattattat   1080
gagctgtacc ctactatgac tgtagtagtt gtgtcagtgg ccacgttcat actcctgtcg   1140
atggtgggta tggcagcggg gatgtgcatg tgtgcacgac gcagatgcat cacaccgtat   1200
gaactgacac caggagctac cgtcccttc ctgcttagcc taatatgctg catcagaaca   1260
gctaaagcg                                                          1269

<210> SEQ ID NO 11
<211> LENGTH: 423
<212> TYPE: PRT
<213> ORGANISM: Chikungunya virus

<400> SEQUENCE: 11

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Ser His Asp Trp
    50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
    130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp Arg Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asp Glu
        195                 200                 205

Gly Leu Thr Thr Thr Asp Lys Val Ile Asn Asn Cys Lys Val Asp Gln
    210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270
```

```
Asn Pro Thr Val Thr Tyr Gly Lys Asn Gln Val Ile Met Leu Leu Tyr
            275                 280                 285

Pro Asp His Pro Thr Leu Leu Ser Tyr Arg Asn Met Gly Glu Glu Pro
    290                 295                 300

Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro Thr Met Thr Val
        355                 360                 365

Val Val Val Ser Val Ala Thr Phe Ile Leu Leu Ser Met Val Gly Met
    370                 375                 380

Ala Ala Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
            420

<210> SEQ ID NO 12
<211> LENGTH: 1260
<212> TYPE: DNA
<213> ORGANISM: Chikungunya virus

<400> SEQUENCE: 12
agcaccaagg acaacttcaa tgtctataaa gccacaagac catacttagc tcactgtccc    60
gactgtggag aagggcactc gtgccatagt cccgtagcac tagaacgcat cagaaatgaa   120
gcgacagacg ggacgctgaa atccaggtc tccttgcaaa tcggaataaa gacggatgat   180
agccacgatt ggaccaagct gcgttatatg acaaccaca tgccagcaga cgcagagagg   240
gcggggctat ttgtaagaac atcagcaccg tgtacgatta ctggaacaat gggacacttc   300
atcctggccc gatgtccaaa aggggaaact ctgacggtgg gattcactga cagtaggaag   360
attagtcact catgtacgca cccatttcac acgacccctc ctgtgatagg tcgggaaaaa   420
ttccattccc gaccgcagca cggtaaagag ctaccttgca gcacgtacgt gcagagcacc   480
gccgcaacta ccgaggagat agaggtacac atgcccccag acacccctga tcgcacatta   540
atgtcacaac agtccggcaa cgtaaagatc acagtcaatg ccagacggt gcggtacaag   600 tgtaattgcg gtggctcaga tgaaggacta caactacag acaaagtgat taataactgc   660
aaggttgatc aatgtcatgc cgcggtcacc aatcacaaaa agtggcagta taactcccct   720
ctggtcccgc gtaatgctga acttgggac cgaaaaggaa aaattcacat cccgtttccg   780
ctggcaaatg taacatgcag ggtgcctaaa gcaaggaacc ccaccgtgac gtacgggaaa   840
aaccaagtca tcatgctact gtatcctgac acccaacac tcctgtccta ccggaatatg   900
ggagaagaac caaactatca agaagagtgg gtgatgcata agaaggaagt cgtgctaacc   960
gtgccgactg aagggctcga ggtcacgtgg ggcaacaacg agccgtataa gtattggccg  1020
cagttatcta caaacggtac agcccatggc cacccgcatg agataattct gtattattat  1080
gagctgtacc ccactatgac tgtagtagtt gtgtcagtgg ccacgttcat actcctgtcg  1140
atggtgggta tggcagcggg gatgtgcatg tgtgcacgac gcagatgcat cacaccgtat  1200
gaactgacac caggagctac cgtcccttc ctgcttagcc taatatgctg catcagaaca  1260
```

```
<210> SEQ ID NO 13
<211> LENGTH: 26
<212> TYPE: PRT
<213> ORGANISM: Sindbis virus

<400> SEQUENCE: 13

Val Tyr Thr Ile Leu Ala Val Ala Ser Ala Thr Val Ala Met Met Ile
1               5                   10                  15

Gly Val Thr Val Ala Val Leu Cys Ala Cys
            20                  25

<210> SEQ ID NO 14
<211> LENGTH: 26
<212> TYPE: PRT
<213> ORGANISM: Chikungunya virus

<400> SEQUENCE: 14

Thr Met Thr Val Val Ile Val Ser Val Ala Ser Phe Val Leu Leu Ser
1               5                   10                  15

Met Val Gly Thr Ala Val Gly Met Cys Val
            20                  25

<210> SEQ ID NO 15
<211> LENGTH: 413
<212> TYPE: PRT
<213> ORGANISM: Chikungunya virus

<400> SEQUENCE: 15

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Ile Asp Gln
    210                 215                 220
```

Cys His Ala Ala Val Thr Asn His Lys Asn Trp Gln Tyr Asn Ser Pro
225                 230                 235                 240

Leu Val Pro Arg Asn Ala Glu Leu Gly Asp Arg Lys Gly Lys Ile His
            245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Thr Met Leu Leu Tyr
            275                 280                 285

Pro Asp His Pro Thr Leu Leu Ser Tyr Arg Asn Met Gly Gln Glu Pro
            290                 295                 300

Asn Tyr His Glu Glu Trp Val Thr His Lys Lys Glu Val Thr Leu Thr
305                 310                 315                 320

Val Pro Thr Glu Gly Leu Glu Val Thr Trp Gly Asn Asn Glu Pro Tyr
            325                 330                 335

Lys Tyr Trp Pro Gln Met Ser Thr Asn Gly Thr Ala His Gly His Pro
            340                 345                 350

His Glu Ile Ile Leu Tyr Tyr Tyr Glu Leu Tyr Pro Thr Met Thr Val
            355                 360                 365

Val Ile Val Val Gly Thr Ala Val Gly Met Cys Val Cys Ala Arg Arg
370                 375                 380

Arg Cys Ile Thr Pro Tyr Glu Leu Thr Pro Gly Ala Thr Val Pro Phe
385                 390                 395                 400

Leu Leu Ser Leu Leu Cys Cys Val Arg Thr Thr Lys Ala
            405                 410

<210> SEQ ID NO 16
<211> LENGTH: 1239
<212> TYPE: DNA
<213> ORGANISM: Chikungunya virus

<400> SEQUENCE: 16
agtactaagg acaattttaa tgtctataaa gccacaagac catatctagc tcattgtcct      60
gactgcggag aagggcattc gtgccacagc cctatcgcat tggagcgcat cagaaatgaa     120
gcaacgacg gaacgctgaa atccaggtc tctttgcaga tcgggataaa gacagatgac      180
agccacgatt ggaccaagct cgctatatg gatagccata cgccagcgga cgcggagcga      240
gccggattgc ttgtaaggac ttcagcaccg tgcacgatca ccgggaccat gggacacttt     300
attctcgccc gatgcccgaa aggagagacg ctgacagtgg gatttacgga cagcagaaag     360
atcagccaca catgcacaca cccgttccat catgaaccac ctgtgatagg tagggagagg     420
ttccactctc gaccacaaca tggtaaagag ttaccttgca gcacgtacgt gcagagcacc     480
gctgccactg ctgaggagat agaggtgcat atgccccag atactcctga ccgcacgctg      540
atgacgcagc agtctggcaa cgtgaagatc acagttaatg gcagacggt gcggtacaag      600
tgcaactgcg gtggctcaaa cgagggactg acaaccacag acaaagtgat caataactgc      660
aaaattgatc agtgccatgc tgcagtcact aatcacaaga attggcaata caactcccct      720
ttagtcccgc gcaacgctga actcgggac cgtaaaggaa agatccacat cccattccca      780
ttggcaaacg tgacttgcag agtgccaaaa gcaagaaacc ctacagtaac ttacggaaaa     840
aaccaagtca ccatgctgct gtatcctgac catccgacac tcttgtctta ccgtaacatg     900
ggacaggaac caaattacca cgaggagtgg gtgacacaca agaaggaggt taccttgacc     960
gtgcctactg agggtctgga ggtcacttgg ggcaacaacg aaccatacaa gtactggccg    1020
cagatgtcta cgaacggtac tgctcatggt cacccacatg agataatctt gtactattat    1080

```
gagctgtacc ccactatgac tgtagtcatt gtggtgggca cagcagtggg aatgtgtgtg   1140
tgcgcacggc gcagatgcat tacaccatat gaattaacac caggagccac tgttcccttc   1200
ctgctcagcc tgctatgctg cgtcagaacg accaaggcg                          1239
```

<210> SEQ ID NO 17
<211> LENGTH: 413
<212> TYPE: PRT
<213> ORGANISM: Chikungunya virus

<400> SEQUENCE: 17

```
Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Ile Asp Gln
    210                 215                 220

Cys His Ala Ala Val Thr Asn His Lys Asn Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Thr Met Leu Leu Tyr
        275                 280                 285

Pro Asp His Pro Thr Leu Leu Ser Tyr Arg Asn Met Gly Gln Glu Pro
    290                 295                 300

Asn Tyr His Glu Glu Trp Val Thr His Lys Lys Glu Val Thr Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Met Ser Thr Asn Gly Thr Ala His Gly His Pro
```

```
                340               345                350
His Glu Ile Ile Leu Tyr Tyr Tyr Glu Leu Tyr Pro Thr Met Thr Val
            355                360                365

Val Ile Val Ser Val Thr Ala Val Gly Met Cys Val Cys Ala Arg Arg
        370                375                380

Arg Cys Ile Thr Pro Tyr Glu Leu Thr Pro Gly Ala Thr Val Pro Phe
385                390                395                400

Leu Leu Ser Leu Leu Cys Cys Val Arg Thr Thr Lys Ala
                405                410

<210> SEQ ID NO 18
<211> LENGTH: 1239
<212> TYPE: DNA
<213> ORGANISM: Chikungunya virus

<400> SEQUENCE: 18
agtactaagg acaattttaa tgtctataaa gccacaagac catatctagc tcattgtcct    60
gactgcggag aagggcattc gtgccacagc cctatcgcat ggagcgcat cagaaatgaa    120
gcaacggacg gaacgctgaa atccaggtc tctttgcaga tcgggataaa gacagatgac    180
agccacgatt ggaccaagct gcgctatatg atagccata cgccagcgga cgcggagcga    240
gccggattgc ttgtaaggac ttcagcaccg tgcacgatca ccgggaccat gggacacttt    300
attctcgccc gatgccgaa aggagagacg ctgacagtgg gatttacgga cagcagaaag    360
atcagccaca catgcacaca cccgttccat catgaaccac ctgtgatagg tagggagagg    420
ttccactctc gaccacaaca tggtaaagag ttaccttgca gcacgtacgt gcagagcacc    480
gctgccactg ctgaggagat agaggtgcat atgccccag atactcctga ccgcacgctg    540
atgacgcagc agtctggcaa cgtgaagatc acagttaatg gcagacggt gcggtacaag    600
tgcaactgcg gtggctcaaa cgagggactg acaaccacag acaaagtgat caataactgc    660
aaaattgatc agtgccatgc tgcagtcact aatcacaaga attggcaata caactcccct    720
ttagtcccgc gcaacgctga actcgggac cgtaaaggaa agatccacat cccattccca    780
ttggcaaacg tgacttgcag agtgccaaaa gcaagaaacc ctacagtaac ttacggaaaa    840
aaccaagtca ccatgctgct gtatcctgac catccgacac tcttgtctta ccgtaacatg    900
ggacaggaac caaattacca cgaggagtgg gtgacacaca gaaggaggt taccttgacc    960
gtgcctactg agggtctgga ggtcacttgg ggcaacaacg aaccatacaa gtactggccg    1020
cagatgtcta cgaacggtac tgctcatggt cacccacatg ataatcttg tactattat    1080
gagctgtacc ccactatgac tgtagtcatt gtgtcggtga cagcagtggg aatgtgtgtg    1140
tgcgcacggc gcagatgcat taccatat gaattaacac caggagccac tgttcccttc    1200
ctgctcagcc tgctatgctg cgtcagaacg accaaggcg                          1239

<210> SEQ ID NO 19
<211> LENGTH: 413
<212> TYPE: PRT
<213> ORGANISM: Chikungunya virus

<400> SEQUENCE: 19

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
```

```
            35                  40                  45
Gln Val Ser Leu Gln Ile Gly Ile Lys Thr Asp Asp Ser His Asp Trp
 50                  55                  60
Thr Lys Leu Arg Tyr Met Asp Ser His Thr Pro Ala Asp Ala Glu Arg
 65                  70                  75                  80
Ala Gly Leu Leu Val Arg Thr Ser Ala Pro Cys Thr Ile Thr Gly Thr
                 85                  90                  95
Met Gly His Phe Ile Leu Ala Arg Cys Pro Lys Gly Glu Thr Leu Thr
                100                 105                 110
Val Gly Phe Thr Asp Ser Arg Lys Ile Ser His Thr Cys Thr His Pro
                115                 120                 125
Phe His His Glu Pro Pro Val Ile Gly Arg Glu Arg Phe His Ser Arg
                130                 135                 140
Pro Gln His Gly Lys Glu Leu Pro Cys Ser Thr Tyr Val Gln Ser Thr
145                 150                 155                 160
Ala Ala Thr Ala Glu Glu Ile Glu Val His Met Pro Pro Asp Thr Pro
                165                 170                 175
Asp Arg Thr Leu Met Thr Gln Gln Ser Gly Asn Val Lys Ile Thr Val
                180                 185                 190
Asn Gly Gln Thr Val Arg Tyr Lys Cys Asn Cys Gly Gly Ser Asn Glu
                195                 200                 205
Gly Leu Thr Thr Thr Asp Lys Val Ile Asn Asn Cys Lys Ile Asp Gln
210                 215                 220
Cys His Ala Ala Val Thr Asn His Lys Asn Trp Gln Tyr Asn Ser Pro
225                 230                 235                 240
Leu Val Pro Arg Asn Ala Glu Leu Gly Asp Arg Lys Gly Lys Ile His
                245                 250                 255
Ile Pro Phe Pro Leu Ala Asn Val Thr Cys Arg Val Pro Lys Ala Arg
                260                 265                 270
Asn Pro Thr Val Thr Tyr Gly Lys Asn Gln Val Thr Met Leu Leu Tyr
                275                 280                 285
Pro Asp His Pro Thr Leu Leu Ser Tyr Arg Asn Met Gly Gln Glu Pro
                290                 295                 300
Asn Tyr His Glu Glu Trp Val Thr His Lys Lys Glu Val Thr Leu Thr
305                 310                 315                 320
Val Pro Thr Glu Gly Leu Glu Val Thr Trp Gly Asn Asn Glu Pro Tyr
                325                 330                 335
Lys Tyr Trp Pro Gln Met Ser Thr Asn Gly Thr Ala His Gly His Pro
                340                 345                 350
His Glu Ile Ile Leu Tyr Tyr Tyr Glu Leu Tyr Pro Thr Met Thr Val
                355                 360                 365
Val Ile Val Ser Gly Thr Ala Val Gly Met Cys Val Cys Ala Arg Arg
                370                 375                 380
Arg Cys Ile Thr Pro Tyr Glu Leu Thr Pro Gly Ala Thr Val Pro Phe
385                 390                 395                 400
Leu Leu Ser Leu Leu Cys Cys Val Arg Thr Thr Lys Ala
                405                 410

<210> SEQ ID NO 20
<211> LENGTH: 1239
<212> TYPE: DNA
<213> ORGANISM: Chikungunya virus

<400> SEQUENCE: 20
```

-continued

| | |
|---|---|
| agtactaagg acaattttaa tgtctataaa gccacaagac catatctagc tcattgtcct | 60 |
| gactgcggag aagggcattc gtgccacagc cctatcgcat tggagcgcat cagaaatgaa | 120 |
| gcaacggacg gaacgctgaa aatccaggtc tctttgcaga tcgggataaa gacagatgac | 180 |
| agccacgatt ggaccaagct gcgctatatg gatagccata cgccagcgga cgcggagcga | 240 |
| gccggattgc ttgtaaggac ttcagcaccg tgcacgatca ccgggaccat gggacacttt | 300 |
| attctcgccc gatgcccgaa aggagagacg ctgacagtgg gatttacgga cagcagaaag | 360 |
| atcagccaca catgcacaca cccgttccat catgaaccac ctgtgatagg tagggagagg | 420 |
| ttccactctc gaccacaaca tggtaaagag ttaccttgca gcacgtacgt gcagagcacc | 480 |
| gctgccactg ctgaggagat agaggtgcat atgcccccag atactcctga ccgcacgctg | 540 |
| atgacgcagc agtctggcaa cgtgaagatc acagttaatg gcagacggt gcggtacaag | 600 |
| tgcaactgcg gtggctcaaa cgagggactg acaaccacac acaaagtgat caataactgc | 660 |
| aaaattgatc agtgccatgc tgcagtcact aatcacaaga attggcaata caactcccct | 720 |
| ttagtcccgc gcaacgctga actcgggac cgtaaaggaa agatccacat cccattccca | 780 |
| ttggcaaacg tgacttgcag agtgccaaaa gcaagaaacc ctacagtaac ttacggaaaa | 840 |
| aaccaagtca ccatgctgct gtatcctgac catccgacac tcttgtctta ccgtaacatg | 900 |
| ggacaggaac caaattacca cgaggagtgg gtgacacaca gaaggaggt taccttgacc | 960 |
| gtgcctactg agggtctgga ggtcacttgg ggcaacaacg aaccatacaa gtactggccg | 1020 |
| cagatgtcta cgaacggtac tgctcatggt cacccacatg agataatctt gtactattat | 1080 |
| gagctgtacc ccactatgac tgtagtcatt gtgtcgggca cagcagtggg aatgtgtgtg | 1140 |
| tgcgcacggc gcagatgcat tacaccatat gaattaacac caggagccac tgttcccttc | 1200 |
| ctgctcagcc tgctatgctg cgtcagaacg accaaggcg | 1239 |

<210> SEQ ID NO 21
<211> LENGTH: 13826
<212> TYPE: DNA
<213> ORGANISM: Chikungunya virus

<400> SEQUENCE: 21

| | |
|---|---|
| atggctgcgt gagacacacg tagcctacca gtttcttact gctctactct gcttagcaag | 60 |
| agacttgaga acccatcatg gatcccgtgt acgtggacat agacgccgac agcgcctttt | 120 |
| taaaggccct gcagcgtgcg taccccatgt ttgaggtgga accaaggcag gtcacaccga | 180 |
| atgaccatgc caatgctaga gcattctcgc atctagctat aaaactaata gagcaggaaa | 240 |
| ttgatcccga ctcaaccatc ctggacatag gcagcgcgcc agcaaggagg atgatgtcgg | 300 |
| ataggaagta ccactgcgtt tgccctatgc gcagcgcaga agaccctgag agactcgcca | 360 |
| actacgcgag aaaactagca tctgccgcag gaaaagtctt ggacagaaac atctccgaaa | 420 |
| aaattggaga tctacaagca gtaatggctg taccagacgc agaaacgccc acattctgct | 480 |
| tgcacactga cgtctcatgt agacaaaggg cggacgtcgc tatataccag gatgtctacg | 540 |
| ccgtgcatgc accaacatcg ctgtaccacc aggcgattaa aggagtccgt gtagcatact | 600 |
| ggataggggtt tgatacaacc ccgttcatgt ataatgccat gcaggtgca taccctcgt | 660 |
| actcgacaaa ctgggcagat gagcaggtgc tgaaggcaaa gaacatagga ttatgttcaa | 720 |
| cagacctgac ggaaggtaga cgaggtaaat tgtctatcat gagaggaaaa aagatgaagc | 780 |
| catgtgaccg gtactgttc tcagtcgggt caacgctta cccggagagc cgtaagcttc | 840 |
| ttaagagttg gcacttacct tcagtgttcc atctaaaagg gaagctcagc ttcacgtgcc | 900 |

```
gctgtgatac agtggtttcg tgtgaaggct atgtcgttaa gagaataacg attagcccgg    960
gcctctacgg taaaaccaca gggtacgcag taacccacca tgcagacgga ttcctaatgt   1020
gcaaaacaac cgatacggta gatggcgaga gagtgtcatt ttcggtatgc acgtacgtac   1080
ccgcaaccat ttgtgatcaa atgacaggta ttccttgcca cggaggttaca ccggaggatg   1140 cacagaagct gctggtggga ctgaaccaga ggatagtggt caatggcaga acgcagagga   1200
acacgaacac aatgaagaat tacttgcttc ctgtagttgc ccaagccctc agtaagtggg   1260
caaaggaatg ccggaaagat atggaagatg aaaaactttt gggcatcaga gaaaggacac   1320
tgacatgctg ctgcctttgg gcgttcaaga agcagaagac acacgggtc tacaagaggc    1380 ctgacactca gtcaattcag aaagtcccag ccgaatttga cagctttgtg gtaccaagtc   1440
tgtggtcatc tggactgtcg atcccgctac ggaccagaat caagtggctg ctaagcaaag   1500
tgccaaagac tgatttgatc ccttacagcg gtgacgccaa agaagcccgc gacgctgaaa   1560
aagaagcaga agaagaacga gaagcggagc taactcgcga ggcactacca ccactacagg   1620
cggcacagga cgacgtccag gtcgaaattg acgtggaaca gctcgaagac agagctgggg   1680
caggaataat tgaaactcca agaggagcta tcaaagtcac tgcccaacca acagaccacg   1740
tcgtgggaga gtacttggta cttttcccgc agaccgtgtt acgaagccag aagctcagcc   1800
tgatccacgc attggcggaa caagtgaaga catgcacaca cagcggacgg gcaggaaggt   1860
acgcggtcga agcatatgac ggcagaatcc ttgtgccctc aggctatgca atatcacctg   1920
aagacttcca gagcctgagc gaaagtgcga cgatggtgta caacgaaagg gagttcgtaa   1980
ataggaaatt acaccatatc gcgttgcacg gaccagccct gaacactgac gaggagtcgt   2040
acgagctggt aagggcagaa aggacagagc atgagtacgt ctatgatgtg gaccaaagaa   2100
ggtgctgcaa gaaagaggag gcagccgggc tggtactggt cggcgacttg accaacccgc   2160
cctaccatga gttcgcatat gaagggctga gaatccgccc cgcctgccca tacaagaccg   2220
cagtaatagg ggtctttgga gtgccaggat ccggcaaatc agcaatcatt aagaacctag   2280
ttaccaggca agacctagtg accagtggaa agaaagaaaa ctgccaagaa atctccaccg   2340
acgtgatgcg acagaggaac ctggagatat ctgcacgcac ggtcgactca ctgctcttga   2400
acggatgcaa tagaccagtc gacgtgttgt acgtcgacga agcttttgcg tgccattctg   2460
gcacgctact tgctctgata gccttggtga gaccgaggca gaaagtcgtg ctatgcggtg   2520
atccgaaaca gtgcggcttc ttcaatatga tgcagatgaa agttaactac aaccataaca   2580
tctgcaccca agtgtaccat aaaagtattt ccaggcggtg tacactgcct gtgactgcca   2640
ttgtgtcctc gttgcattac gaaggcaaaa tgcgcacaac aaatgagtac aacaagccaa   2700
ttgtagtgga tactacaggc tcgacaaaac ccgaccccgg agaccttgtg ctaacatgtt   2760
tcagagggtg ggttaagcaa ctgcaaattg actatcgtgg acacgaggtc atgacagcag   2820
ctgcatctca ggggctaacc agaaaagggg tctatgccgt caggcaaaaa gttaatgaaa   2880 accccctta cgcatcaaca tcagagcacg tgaacgtgct actgacgcgt acggaaggca   2940
aactagtatg gaagacactt tctggagacc catggataaa gacactgcag aacccgccga   3000
aaggaaattt taaagcaaca attaaggaat gggaagtgga acatgcttca ataatggcgg   3060
gtatctgtaa ccaccaagtg accttgaca cgttccagaa taaagccaat gtctgctggg   3120
cgaagagctt agtccccatc ctagaaacag cagggataaa attaaacgac aggcagtggt   3180
cccagataat ccaggctttt aaagaagaca gagcatactc acccgaggtg gccctgaatg   3240
```

```
agatatgcac gcgcatgtac ggggtagacc tggacagcgg actgttctct aaaccactgg    3300
tgtccgtgca tcatgcggat aatcactggg acaacaggcc gggagggaag atgttcggat    3360
tcaaccccga agcggcgtcc atactggaga ggaaataccc gtttacaaaa gggaagtgga    3420
ataccaacaa gcaaatctgt gtgactacta ggaggattga agattttaac ccgaacacca    3480
acattatacc tgccaacagg agattaccgc attcattggt ggccgaacat cgcccggtaa    3540
aaggggagag gatggaatgg ttggtcaaca aaataaatgg ccaccatgtg ctcctggtca    3600
gcggctacaa cctcgttctg cccactaaga gagtcacctg ggtggcgccg ctgggcattc    3660
ggggagctga ctacacatac aacctagagt taggcctacc agcaacgctc ggtagatatg    3720
acctagtgat tataaacatc cacacaccct ttcgcataca tcattaccaa cagtgcgtgg    3780
atcacgcaat gaagctgcag atgctcggag gagactccct gagactgctc aagccgggtg    3840
gttcattact gatcagggca tacggctacg cagacagaac aagcgaacga gtagtctgcg    3900
tattgggacg caagtttcga tcatccagag cgttgaaacc gccgtgcgtc actagcaaca    3960
ccgagatgtt tttcttgttc agcaactttg ataacggcag aaggaacttt acgacgcacg    4020
taatgaacaa ccagctgaat gctgcttttg ttggtcaggc cacccgagca gggtgcgcac    4080
cgtcgtaccg ggttaaacgc atggacatcg caaagaacga tgaagagtgt gtagtcaacg    4140
ccgccaaccc tcgtgggcta ccaggcgatg gcgtctgtaa agcagtatac aaaaaatggc    4200
cggagtcctt caagaacagt gcaacaccag tgggaaccgc aaagacagtc atgtgcggta    4260
catacccggt aatccatgca gtaggaccta atttctcaaa ttactctgag tccgaaggag    4320
accgggaatt ggcagctgct taccgagaag tcgctaagga ggtgactaga ctaggagtaa    4380
acagcgtagc tataccgctc ctttccaccg gtgtgtactc tggagggaaa gacaggctga    4440
ctcagtcact aaaccaccct tttacagcat tagactcaac tgatgcagat gtggttatct    4500
actgccgcga caaggagtgg gagaagaaaa tagctgaggc catacaaatg aggacccaag    4560
tggaattact agacgaacac atctctgtag actgcgatat catccgagtg caccctgaca    4620
gcagtttggc aggtagaaaa gggtacagca ctacagaagg ttcactgtac tcctacttgg    4680
aagggacacg gttccatcag acggcagtgg acatggcaga agtatacacc atgtggccaa    4740
agcagacgga ggctaatgaa caagtttgct tgtacgcatt gggggaaagt atagaatcaa    4800
tcaggcaaaa gtgcccagtg gatgacgcag atgcatcgtc gcccccaaaa accgtcccgt    4860
gcctctgccg ttatgccatg acacccgaac gagtcaccag gcttcgtatg aaccatgtca    4920
caagcataat agtatgctca tcattccccc ttccaaagta taaaatagaa ggagtgcaga    4980
aagtcaagtg ttctaaagtg atgctgttcg accataacgt gccatcacgc gttagtccaa    5040
gggaatataa atcgcctcag gagaccgcac aagaagtaag ttcgaccacg tcactgacgc    5100
acagccaatt cgaccttagc gttgacggtg aggaactgcc cgctccgtct gacttggaag    5160
ctgacgctcc gattccggaa ccaacaccag acgacagagc ggtacttact ttgcctccca    5220
cgattgataa ttttttcggct gtgtcagact gggtaatgaa taccgcgcca gtcgcaccac    5280
ccagaagaag acgtgggaaa aacttgaatg tcacctgcga cgagagagaa gggaacgtac    5340
ttcccatggc tagcgttcgg ttcttcagag cggatctgca ctccatcgta caggaaacgg    5400
cagagatacg cgatacggcc gcgtccctcc aggcgcccct gagtgtcgct acagaaccga    5460
atcaactgcc gatctcattt ggagcaccaa acgagacttt ccccataacg ttcgggattt    5520 tgatgaagg ggagattgaa agcttgtcct ctgagttact gacctttggg gacttctcgc    5580
cgggcgaagt ggatgacctg acagacagcg actggtccac gtgttcagac acggacgacg    5640
```

```
aattatgact agataggcca ggtgggtaca tattctcatc tgacaccggc cccggccacc      5700
tgcaacagag gtctgtccgt cagacagtac tgccggtaaa taccttggag gaagttcagg      5760
aggagaaatg ttacccacct aagttggatg aagtgaaaga gcagttgtta cttaagaaac      5820
tccaggaaag tgcgtccatg gctaacagaa gcaggtacca atcccgcaaa gtagagaaca      5880
tgaaagcaac aatagtccaa aggctgaagg gtggttgcaa actttattta atgtcggaga      5940
ccccgaaagt tcctacctac cgaactacat atccggcacc agtgtactca cccccaatca      6000
atatccgact gtccaacccc gagtctgctg tggcagcgtg caatgagttc ctagcaagga      6060
actatccgac agttgcgtcg taccaaatca ccgatgagta cgatgcatac ctagacatgg      6120
tggacgggtc ggaaagttgc cttgaccggg cgacgttcaa cccatcaaag cttagaagtt      6180
atccaaaaca gcactcctac catgcaccca caatcagaag tgccgtacct tcccgttcc      6240 agaacacgct gcagaacgta ctggctgctg ccacgaaaag aaattgcaac gtcacacaga      6300
tgagagaact gcctactttg gattcagcgg tatttaatgt tgagtgcttt aaaaaatttg      6360
cgtgcaatca agaatactgg aaggaatttg ccgccagccc tattaggata acgactgaga      6420
acttgacaac ttatgtcaca aaactaaaag gaccaaaagc agcagcactg tttgccaaga      6480
cacataacct gctaccactg caggaggtgc cgatggacag gtttactgta gacatgaaaa      6540
gggacgtgaa ggtgactccg gggacgaagc acactgagga aagacctaaa gtgcaggtca      6600
tacaggcagc cgaacctttg gcaacagcat atctgtgtgg gatccacaga gagttggtca      6660
gaaggctgaa tgcagtcctt ctacctaatg tacacacgct gtttgacatg tctgccgagg      6720
actttgacgc cattattgcc gcgcacttca agccggggga cgccgtattg gaaaccgata      6780
tagcctcctt tgacaagagc caagacgact cattggcgct cactgctcta atgttgctag      6840
aggatttggg ggtggatcat cccctgttgg acttgataga ggctgccttc ggggagatct      6900
ccagctgcca cctaccgacg gcacccgtt ttaagttcgg cgccatgatg aagtctggta      6960
tgttcctaac cctgttcgtc aacacactgc taaacatcac catagccagc cgagtgctgg      7020
aggaccgctt gacaaggtct gcgtgcgcgg ccttcatcgg cgacgacaat ataatacatg      7080
gggttgtctc tgacgaactg atggcagcaa ggtgtgctac atggatgaac atggaagtga      7140
agatcataga tgcggtcgtg tctcagaaag ccccgtactt ctgcggaggg tttatactgt      7200
atgacacagt agcaggcacg gcctgcagag tggcagaccc gctaaagcgg ctgttcaagc      7260
tgggcaaacc gctggcagcg ggagatgaac aagacgacga cagaagacgt gcactggctg      7320
acgaagtggt tagatggcaa cgaacaggac taactgatga gctagaaaaa gcggtacact      7380
ccaggtatga agtgcagggc atatctgtcg tggtaatgtc tatggccacc tttgcaagct      7440
ctagatctaa ctttgagaag ctcagaggac cgtcgtaac cctgtacggt ggtcctaaat      7500
aggtacgcac tacagctacc tatttcgtca gaaaccaatc gcagctactt gcatacctac      7560
cagctacaat ggagttcatc ccgacgcaaa ctttctataa cagaaggtac caaccccgac      7620
cctgggcccc acgccctaca attcaagtaa ttagacctag accacgtcca cagaggcagg      7680
ctgggcaact cgcccagctg atctccgcag tcaacaaatt gaccatgcgc gcggtacctc      7740
aacagaagcc tcgcagaaat cggaaaaaca agaagcaaag gcagaagaag caggcgccgc      7800
aaaacgaccc aaagcaaaag aagcaaccac cacaaaagaa gccggctcaa aagaagaaga      7860
aaccaggccg tagggagaga atgtgcatga aaattgaaaa tgattgcatc ttcgaagtca      7920
agcatgaagg caaagtgatg ggctacgcat gcctggtggg ggataaagta atgaaaccag      7980
```

```
cacatgtgaa gggaactatc gacaatgccg atctggctaa actggccttt aagcggtcgt   8040
ctaaatacga tcttgaatgt gcacagatac cggtgcacat gaagtctgat gcctcgaagt   8100
ttacccacga gaaacccgag gggtactata actggcatca cggagcagtg cagtattcag   8160
gaggccggtt cactatcccg acgggtgcag gcaagccggg agacagcggc agaccgatct   8220
tcgacaacaa aggacgggtg gtggccatcg tcctaggagg ggccaacgaa ggtgcccgca   8280
cggccctctc cgtggtgacg tggaacaaag acatcgtcac aaaaattacc cctgagggag   8340
ccgaagagtg gagcctcgcc ctcccggtct tgtgcctgtt ggcaaacact acattcccct   8400
gctctcagcc gccttgcaca ccctgctgct acgaaaagga accggaaagc accttgcgca   8460
tgcttgagga caacgtgatg agacccggat actaccagct actaaaagca tcgctgactt   8520
gctctcccca ccgccaaaga cgcagtacta aggacaattt taatgtctat aaagccacaa   8580
gaccatatct agctcattgt cctgactgcg gagaagggca ttcgtgccac agccctatcg   8640
cattggagcg catcagaaat gaagcaacgg acgaacgct gaaaatccag gtctctttgc   8700
agatcgggat aaagacagat gacagccacg attggaccaa gctgcgctat atggatagcc   8760
atacgccagc ggacgcggag cgagccggat tgcttgtaag gacttcagca ccgtgcacga   8820
tcaccgggac catgggacac tttattctcg cccgatgccc gaaaggagag acgctgacag   8880
tgggatttac ggacagcaga aagatcagcc acacatgcac acaccgttc catcatgaac   8940 cacctgtgat aggtagggag aggttccact ctcgaccaca acatggtaaa gagttacctt   9000
gcagcacgta cgtgcagagc accgctgcca ctgctgagga gatagaggtg catatgcccc   9060
cagatactcc tgaccgcacg ctgatgacgc agcagtctgg caacgtgaag atcacagtta   9120
atgggcagac ggtgcggtac aagtgcaact gcggtggctc aaacgaggga ctgacaacca   9180
cagacaaagt gatcaataac tgcaaaattg atcagtgcca tgctgcagtc actaatcaca   9240
agaattggca atacaactcc cctttagtcc cgcgcaacgc tgaactcggg gaccgtaaag   9300
gaaagatcca catcccattc ccattggcaa acgtgacttg cagagtgcca aaagcaagaa   9360
accctacagt aacttacgga aaaaaccaag tcaccatgct gctgtatcct gaccatccga   9420
cactcttgtc ttaccgtaac atgggacagg aaccaaatta ccacgaggag tgggtgacac   9480
acaagaagga ggttaccttg accgtgccta ctgagggtct ggaggtcact tggggcaaca   9540
acgaaccata caagtactgg ccgcagatgt ctacgaacgg tactgctcat ggtcacccac   9600
atgagataat cttgtactat tatgagctgt accccactat gactgtagtc attgtgtcgg   9660
tggcctcgtt cgtgcttctg tcgatggtgg gcacagcagt gggaatgtgt gtgtgcgcac   9720
ggcgcagatg cattacacca tatgaattaa caccaggagc cactgttccc ttcctgctca   9780
gcctgctatg ctgcgtcaga acgaccaagg cggccacata ttacgaggct gcggcatatc   9840 tatgaacga acagcagccc ctgttctggt tgcaggctct tatcccgctg ccgccttga   9900 tcgtcctgtg caactgtctg aaactcttgc catgctgctg taagaccctg gctttttag   9960 ccgtaatgag catcggtgcc cacactgtga gcgcgtacga acacgtaaca gtgatcccga   10020
acacggtggg agtaccgtat aagactcttg tcaacagacc gggttacagc cccatggtgt   10080
tggagatgga gctacaatca gtcacccttgg aaccaacact gtcacttgac tacatcacgt   10140
gcgagtacaa aactgtcatc ccctcccgt acgtgaagtg ctgtggtaca gcagagtgca   10200
aggacaagag cctaccagac tacagctgca aggtctttac tggagtctac ccatttatgt   10260
ggggcggcgc ctactgcttt tgcgacgccg aaaaatacgca attgagcgag gcacatgtag   10320
agaaatctga atcttgcaaa acagagtttg catcggccta cagagcccac accgcatcgg   10380
```

```
cgtcggcgaa gctccgcgtc ctttaccaag gaaacaacat taccgtagct gcctacgcta   10440
acggtgacca tgccgtcaca gtaaaggacg ccaagtttgt cgtgggccca atgtcctccg   10500
cctggacacc ttttgacaac aaaatcgtgg tgtacaaagg cgacgtctac aacatggact   10560 acccacctt tggcgcagga agaccaggac aatttggtga cattcaaagt cgtacaccgg   10620
aaagtaaaga cgtttatgcc aacactcagt tggtactaca gaggccagca gcaggcacgg   10680
tacatgtacc atactctcag gcaccatctg gcttcaagta ttggctgaag gaacgaggag   10740
catcgctaca gcacacggca ccgttcggtt gccagattgc gacaaacccg gtaagagctg   10800
taaattgcgc tgtggggaac ataccaattt ccatcgacat accggatgcg gcctttacta   10860
gggttgtcga tgcaccctct gtaacggaca tgtcatgcga agtaccagcc tgcactcact   10920
cctccgactt tggggggcgtc gccatcatca aatacacagc tagcaagaaa ggtaaatgtg   10980
cagtacattc gatgaccaac gccgttacca ttcgagaagc cgacgtagaa gtagagggga   11040
actcccagct gcaaatatcc ttctcaacag ccctggcaag cgccgagttt cgcgtgcaag   11100
tgtgctccac acaagtacac tgcgcagccg catgccaccc tccaaaggac cacatagtca   11160
attacccagc atcacacacc acccttgggg tccaggatat atccacaacg gcaatgtctt   11220
gggtgcagaa gattacggga ggagtaggat taattgttgc tgttgctgcc ttaattttaa   11280
ttgtggtgct atgcgtgtcg tttagcaggc actaaaccga tgataaggca cgaaataact   11340
aaatagcaaa agtagaaagt acataaccag gtatatgtgc cccttaagag gcacaatata   11400
tatagctaag cactattaga tcaaagggct atacaacccc tgaatagtaa caaaacacaa   11460
aaaccaataa aaatcataaa aagaaaaatc tcataaacag gtataagtgt cccctaagag   11520
acacattgta tgtaggtagt aagtatagat caaagggcta tattaacccc tgaatagtaa   11580
caaaacacaa aaacaataaa aactacaaaa tagaaaatct ataaacaaaa gtagttcaaa   11640
gggctacaaa accctgaat agtaacaaaa cataaaatgt aataaaaatt aagtgtgtac   11700
ccaaaagagg tacagtaaga atcagtgaat atcacaattg gcaacgagaa gagacgtagg   11760
tatttaagct tcctaaaagc agccgaactc actttgagac gtaggcatag cataccgaac   11820
tcttccacta ttctccgaac ccacagggac gtaggagatg ttattttgtt tttaatattt   11880
caaaaaaaaa aaaaaaaaaa aaaaaaaaaa aaaaaaaaa agcggccgct taattaatcg   11940
aggggaatta attcttgaag acgaaagggc caggtggcac ttttcgggga aatgtgcgcg   12000
gaacccctat ttgtttattt ttctaaatac attcaaatat gtatccgctc atgagacaat   12060
aaccctgata aatgcttcaa taatattgaa aaaggaagag tatgagtatt caacatttcc   12120
gtgtcgccct tattcccttt tttgcggcat tttgccttcc tgtttttgct cacccagaaa   12180
cgctggtgaa agtaaaagat gctgaagatc agttgggtgc acgagtgggt tacatcgaac   12240
tggatctcaa cagcggtaag atccttgaga gttttcgccc cgaagaacgt tttccaatga   12300
tgagcacttt taaagttctg ctatgtggcg cggtattatc ccgtgttgac gccgggcaag   12360
agcaactcgg tcgccgcata cactattctc agaatgactt ggttgagtac tcaccagtca   12420
cagaaaagca tcttacggat ggcatgacag taagagaatt atgcagtgct gccataacca   12480
tgagtgataa cactgcggcc aacttacttc tgacaacgat cggaggaccg aaggagctaa   12540 ccgcttttt gcacaacatg gggatcatg taactcgcct tgatcgttgg gaaccggagc   12600
tgaatgaagc cataccaaac gacgagcgtg acaccacgat gcctgtagca atggcaacaa   12660
cgttgcgcaa actattaact ggcgaactac ttactctagc ttcccggcaa caattaatag   12720
```

-continued

```
actggatgga ggcggataaa gttgcaggac cacttctgcg ctcggccctt ccggctggct   12780
ggtttattgc tgataaatct ggagccggtg agcgtgggtc tcgcggtatc attgcagcac   12840
tggggccaga tggtaagccc tcccgtatcg tagttatcta cacgacgggg agtcaggcaa   12900
ctatggatga acgaaataga cagatcgctg agataggtgc ctcactgatt aagcattggt   12960
aactgtcaga ccaagtttac tcatatatac tttagattga tttaaaactt cattttttaat   13020 ttaaaaggat ctaggtgaag atccttttg ataatctcat gaccaaaatc ccttaacgtg    13080
agttttcgtt ccactgagcg tcagacccg tagaaaagat caaggatctc tcttgagatc    13140 cttttttttct gcgcgtaatc tgctgcttgc aaacaaaaaa accaccgcta ccagcggtgg   13200
tttgtttgcc ggatcaagag ctaccaactc tttttccgaa ggtaactggc ttcagcagag   13260
cgcagatacc aaatactgtc cttctagtgt agccgtagtt aggccaccac ttcaagaact   13320
ctgtagcacc gcctacatac ctcgctctgc taatcctgtt accagtggct gctgccagtg   13380
gcgataagtc gtgtcttacc gggttggact caagacgata gttaccggat aaggcgcagc   13440
ggtcgggctg aacggggggt tcgtgcacac agcccagctt ggagcgaacg acctacaccg   13500
aactgagata cctacagcgt gagcattgag aaagcgccac gcttcccgaa gggagaaagg   13560
cggacaggta tccggtaagc ggcagggtcg aacaggaga cgcacgagg gagcttccag     13620 ggggaaacgc ctggtatctt tatagtcctg tcgggtttcg ccacctctga cttgagcgtc   13680
gatttttgtg atgctcgtca gggggcgga gcctatggaa aaacgccagc aacgcgagct    13740
cgtatggaca tattgtcgtt agaacgcggc tacaattaat acataacctt atgtatcata   13800
cacaatcgat ttaggtgaca ctatag                                        13826
```

<210> SEQ ID NO 22
<211> LENGTH: 2474
<212> TYPE: PRT
<213> ORGANISM: Chikungunya virus
<220> FEATURE:
<221> NAME/KEY: misc_feature
<222> LOCATION: (1857)..(1857)
<223> OTHER INFORMATION: Xaa can be any naturally occurring amino acid

<400> SEQUENCE: 22

```
Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Glu Lys Ile Gly Asp Leu Gln Ala Val Met Ala Val Pro Asp Ala
        115                 120                 125

Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160
```

```
Ser Leu Tyr His Gln Ala Ile Lys Gly Val Arg Val Ala Tyr Trp Ile
                165                 170                 175
Gly Phe Asp Thr Thr Pro Phe Met Tyr Asn Ala Met Ala Gly Ala Tyr
            180                 185                 190
Pro Ser Tyr Ser Thr Asn Trp Ala Asp Glu Gln Val Leu Lys Ala Lys
        195                 200                 205
Asn Ile Gly Leu Cys Ser Thr Asp Leu Thr Glu Gly Arg Arg Gly Lys
    210                 215                 220
Leu Ser Ile Met Arg Gly Lys Lys Met Lys Pro Cys Asp Arg Val Leu
225                 230                 235                 240
Phe Ser Val Gly Ser Thr Leu Tyr Pro Glu Ser Arg Lys Leu Leu Lys
                245                 250                 255
Ser Trp His Leu Pro Ser Val Phe His Leu Lys Gly Lys Leu Ser Phe
                260                 265                 270
Thr Cys Arg Cys Asp Thr Val Ser Cys Glu Gly Tyr Val Val Lys
            275                 280                 285
Arg Ile Thr Ile Ser Pro Gly Leu Tyr Gly Lys Thr Thr Gly Tyr Ala
        290                 295                 300
Val Thr His His Ala Asp Gly Phe Leu Met Cys Lys Thr Thr Asp Thr
305                 310                 315                 320
Val Asp Gly Glu Arg Val Ser Phe Ser Val Cys Thr Tyr Val Pro Ala
                325                 330                 335
Thr Ile Cys Asp Gln Met Thr Gly Ile Leu Ala Thr Glu Val Thr Pro
            340                 345                 350
Glu Asp Ala Gln Lys Leu Leu Val Gly Leu Asn Gln Arg Ile Val Val
        355                 360                 365
Asn Gly Arg Thr Gln Arg Asn Thr Asn Thr Met Lys Asn Tyr Leu Leu
    370                 375                 380
Pro Val Val Ala Gln Ala Leu Ser Lys Trp Ala Lys Glu Cys Arg Lys
385                 390                 395                 400
Asp Met Glu Asp Glu Lys Leu Leu Gly Ile Arg Glu Arg Thr Leu Thr
                405                 410                 415
Cys Cys Cys Leu Trp Ala Phe Lys Lys Gln Lys Thr His Thr Val Tyr
            420                 425                 430
Lys Arg Pro Asp Thr Gln Ser Ile Gln Lys Val Pro Ala Glu Phe Asp
        435                 440                 445
Ser Phe Val Val Pro Ser Leu Trp Ser Ser Gly Leu Ser Ile Pro Leu
    450                 455                 460
Arg Thr Arg Ile Lys Trp Leu Leu Ser Lys Val Pro Lys Thr Asp Leu
465                 470                 475                 480
Ile Pro Tyr Ser Gly Asp Ala Lys Glu Ala Arg Asp Ala Glu Lys Glu
                485                 490                 495
Ala Glu Glu Glu Arg Glu Ala Glu Leu Thr Arg Glu Ala Leu Pro Pro
            500                 505                 510
Leu Gln Ala Ala Gln Asp Asp Val Gln Val Glu Ile Asp Val Glu Gln
        515                 520                 525
Leu Glu Asp Arg Ala Gly Ala Gly Ile Ile Glu Thr Pro Arg Gly Ala
    530                 535                 540
Ile Lys Val Thr Ala Gln Pro Thr Asp His Val Val Gly Glu Tyr Leu
545                 550                 555                 560
Val Leu Ser Pro Gln Thr Val Leu Arg Ser Gln Lys Leu Ser Leu Ile
                565                 570                 575
```

```
His Ala Leu Ala Glu Gln Val Lys Thr Cys Thr His Ser Gly Arg Ala
                580                 585                 590
Gly Arg Tyr Ala Val Glu Ala Tyr Asp Gly Arg Ile Leu Val Pro Ser
            595                 600                 605
Gly Tyr Ala Ile Ser Pro Glu Asp Phe Gln Ser Leu Ser Glu Ser Ala
        610                 615                 620
Thr Met Val Tyr Asn Glu Arg Glu Phe Val Asn Arg Lys Leu His His
625                 630                 635                 640
Ile Ala Leu His Gly Pro Ala Leu Asn Thr Asp Glu Ser Tyr Glu
                645                 650                 655
Leu Val Arg Ala Glu Arg Thr Glu His Glu Tyr Val Tyr Asp Val Asp
            660                 665                 670
Gln Arg Arg Cys Cys Lys Lys Glu Ala Ala Gly Leu Val Leu Val
        675                 680                 685
Gly Asp Leu Thr Asn Pro Pro Tyr His Glu Phe Ala Tyr Glu Gly Leu
    690                 695                 700
Arg Ile Arg Pro Ala Cys Pro Tyr Lys Thr Ala Val Ile Gly Val Phe
705                 710                 715                 720
Gly Val Pro Gly Ser Gly Lys Ser Ala Ile Ile Lys Asn Leu Val Thr
                725                 730                 735
Arg Gln Asp Leu Val Thr Ser Gly Lys Lys Glu Asn Cys Gln Glu Ile
            740                 745                 750
Ser Thr Asp Val Met Arg Gln Arg Asn Leu Glu Ile Ser Ala Arg Thr
        755                 760                 765
Val Asp Ser Leu Leu Leu Asn Gly Cys Asn Arg Pro Val Asp Val Leu
    770                 775                 780
Tyr Val Asp Glu Ala Phe Ala Cys His Ser Gly Thr Leu Leu Ala Leu
785                 790                 795                 800
Ile Ala Leu Val Arg Pro Arg Gln Lys Val Val Leu Cys Gly Asp Pro
                805                 810                 815
Lys Gln Cys Gly Phe Phe Asn Met Met Gln Met Lys Val Asn Tyr Asn
            820                 825                 830
His Asn Ile Cys Thr Gln Val Tyr His Lys Ser Ile Ser Arg Arg Cys
        835                 840                 845
Thr Leu Pro Val Thr Ala Ile Val Ser Ser Leu His Tyr Glu Gly Lys
    850                 855                 860
Met Arg Thr Thr Asn Glu Tyr Asn Lys Pro Ile Val Val Asp Thr Thr
865                 870                 875                 880
Gly Ser Thr Lys Pro Asp Pro Gly Asp Leu Val Leu Thr Cys Phe Arg
                885                 890                 895
Gly Trp Val Lys Gln Leu Gln Ile Asp Tyr Arg Gly His Glu Val Met
            900                 905                 910
Thr Ala Ala Ala Ser Gln Gly Leu Thr Arg Lys Gly Val Tyr Ala Val
        915                 920                 925
Arg Gln Lys Val Asn Glu Asn Pro Leu Tyr Ala Ser Thr Ser Glu His
    930                 935                 940
Val Asn Val Leu Leu Thr Arg Thr Glu Gly Lys Leu Val Trp Lys Thr
945                 950                 955                 960
Leu Ser Gly Asp Pro Trp Ile Lys Thr Leu Gln Asn Pro Pro Lys Gly
                965                 970                 975
Asn Phe Lys Ala Thr Ile Lys Glu Trp Glu Val Glu His Ala Ser Ile
            980                 985                 990
Met Ala Gly Ile Cys Asn His Gln  Val Thr Phe Asp Thr  Phe Gln Asn
```

```
            995                 1000                1005
Lys Ala Asn Val Cys Trp Ala Lys Ser Leu Val Pro Ile Leu Glu
    1010                1015                1020

Thr Ala Gly Ile Lys Leu Asn Asp Arg Gln Trp Ser Gln Ile Ile
    1025                1030                1035

Gln Ala Phe Lys Glu Asp Arg Ala Tyr Ser Pro Glu Val Ala Leu
    1040                1045                1050

Asn Glu Ile Cys Thr Arg Met Tyr Gly Val Asp Leu Asp Ser Gly
    1055                1060                1065

Leu Phe Ser Lys Pro Leu Val Ser Val His His Ala Asp Asn His
    1070                1075                1080

Trp Asp Asn Arg Pro Gly Gly Lys Met Phe Gly Phe Asn Pro Glu
    1085                1090                1095

Ala Ala Ser Ile Leu Glu Arg Lys Tyr Pro Phe Thr Lys Gly Lys
    1100                1105                1110

Trp Asn Thr Asn Lys Gln Ile Cys Val Thr Thr Arg Arg Ile Glu
    1115                1120                1125

Asp Phe Asn Pro Asn Thr Asn Ile Ile Pro Ala Asn Arg Arg Leu
    1130                1135                1140

Pro His Ser Leu Val Ala Glu His Arg Pro Val Lys Gly Glu Arg
    1145                1150                1155

Met Glu Trp Leu Val Asn Lys Ile Asn Gly His His Val Leu Leu
    1160                1165                1170

Val Ser Gly Tyr Asn Leu Val Leu Pro Thr Lys Arg Val Thr Trp
    1175                1180                1185

Val Ala Pro Leu Gly Ile Arg Gly Ala Asp Tyr Thr Tyr Asn Leu
    1190                1195                1200

Glu Leu Gly Leu Pro Ala Thr Leu Gly Arg Tyr Asp Leu Val Ile
    1205                1210                1215

Ile Asn Ile His Thr Pro Phe Arg Ile His His Tyr Gln Gln Cys
    1220                1225                1230

Val Asp His Ala Met Lys Leu Gln Met Leu Gly Gly Asp Ser Leu
    1235                1240                1245

Arg Leu Leu Lys Pro Gly Gly Ser Leu Leu Ile Arg Ala Tyr Gly
    1250                1255                1260

Tyr Ala Asp Arg Thr Ser Glu Arg Val Val Cys Val Leu Gly Arg
    1265                1270                1275

Lys Phe Arg Ser Ser Arg Ala Leu Lys Pro Pro Cys Val Thr Ser
    1280                1285                1290

Asn Thr Glu Met Phe Phe Leu Phe Ser Asn Phe Asp Asn Gly Arg
    1295                1300                1305

Arg Asn Phe Thr Thr His Val Met Asn Asn Gln Leu Asn Ala Ala
    1310                1315                1320

Phe Val Gly Gln Ala Thr Arg Ala Gly Cys Ala Pro Ser Tyr Arg
    1325                1330                1335

Val Lys Arg Met Asp Ile Ala Lys Asn Asp Glu Glu Cys Val Val
    1340                1345                1350

Asn Ala Ala Asn Pro Arg Gly Leu Pro Gly Asp Gly Val Cys Lys
    1355                1360                1365

Ala Val Tyr Lys Lys Trp Pro Glu Ser Phe Lys Asn Ser Ala Thr
    1370                1375                1380

Pro Val Gly Thr Ala Lys Thr Val Met Cys Gly Thr Tyr Pro Val
    1385                1390                1395
```

-continued

```
Ile His Ala Val Gly Pro Asn Phe Ser Asn Tyr Ser Glu Ser Glu
    1400                1405                1410

Gly Asp Arg Glu Leu Ala Ala Tyr Arg Glu Val Ala Lys Glu
    1415                1420                1425

Val Thr Arg Leu Gly Val Asn Ser Val Ala Ile Pro Leu Leu Ser
    1430                1435                1440

Thr Gly Val Tyr Ser Gly Gly Lys Asp Arg Leu Thr Gln Ser Leu
    1445                1450                1455

Asn His Leu Phe Thr Ala Leu Asp Ser Thr Asp Ala Asp Val Val
    1460                1465                1470

Ile Tyr Cys Arg Asp Lys Glu Trp Glu Lys Lys Ile Ala Glu Ala
    1475                1480                1485

Ile Gln Met Arg Thr Gln Val Glu Leu Leu Asp Glu His Ile Ser
    1490                1495                1500

Val Asp Cys Asp Ile Ile Arg Val His Pro Asp Ser Ser Leu Ala
    1505                1510                1515

Gly Arg Lys Gly Tyr Ser Thr Thr Glu Gly Ser Leu Tyr Ser Tyr
    1520                1525                1530

Leu Glu Gly Thr Arg Phe His Gln Thr Ala Val Asp Met Ala Glu
    1535                1540                1545

Val Tyr Thr Met Trp Pro Lys Gln Thr Glu Ala Asn Glu Gln Val
    1550                1555                1560

Cys Leu Tyr Ala Leu Gly Glu Ser Ile Glu Ser Ile Arg Gln Lys
    1565                1570                1575

Cys Pro Val Asp Asp Ala Asp Ala Ser Ser Pro Lys Thr Val
    1580                1585                1590

Pro Cys Leu Cys Arg Tyr Ala Met Thr Pro Glu Arg Val Thr Arg
    1595                1600                1605

Leu Arg Met Asn His Val Thr Ser Ile Ile Val Cys Ser Ser Phe
    1610                1615                1620

Pro Leu Pro Lys Tyr Lys Ile Glu Gly Val Gln Lys Val Lys Cys
    1625                1630                1635

Ser Lys Val Met Leu Phe Asp His Asn Val Pro Ser Arg Val Ser
    1640                1645                1650

Pro Arg Glu Tyr Lys Ser Pro Gln Glu Thr Ala Gln Glu Val Ser
    1655                1660                1665

Ser Thr Thr Ser Leu Thr His Ser Gln Phe Asp Leu Ser Val Asp
    1670                1675                1680

Gly Glu Glu Leu Pro Ala Pro Ser Asp Leu Glu Ala Asp Ala Pro
    1685                1690                1695

Ile Pro Glu Pro Thr Pro Asp Arg Ala Val Leu Thr Leu Pro
    1700                1705                1710

Pro Thr Ile Asp Asn Phe Ser Ala Val Ser Asp Trp Val Met Asn
    1715                1720                1725

Thr Ala Pro Val Ala Pro Arg Arg Arg Arg Gly Lys Asn Leu
    1730                1735                1740

Asn Val Thr Cys Asp Glu Arg Glu Gly Asn Val Leu Pro Met Ala
    1745                1750                1755

Ser Val Arg Phe Phe Arg Ala Asp Leu His Ser Ile Val Gln Glu
    1760                1765                1770

Thr Ala Glu Ile Arg Asp Thr Ala Ala Ser Leu Gln Ala Pro Leu
    1775                1780                1785
```

```
Ser Val Ala Thr Glu Pro Asn Gln Leu Pro Ile Ser Phe Gly Ala
1790                1795                1800

Pro Asn Glu Thr Phe Pro Ile Thr Phe Gly Asp Phe Asp Glu Gly
1805                1810                1815

Glu Ile Glu Ser Leu Ser Ser Glu Leu Leu Thr Phe Gly Asp Phe
1820                1825                1830

Ser Pro Gly Glu Val Asp Asp Leu Thr Asp Ser Asp Trp Ser Thr
1835                1840                1845

Cys Ser Asp Thr Asp Asp Glu Leu Xaa Leu Asp Arg Ala Gly Gly
1850                1855                1860

Tyr Ile Phe Ser Ser Asp Thr Gly Pro Gly His Leu Gln Gln Arg
1865                1870                1875

Ser Val Arg Gln Thr Val Leu Pro Val Asn Thr Leu Glu Glu Val
1880                1885                1890

Gln Glu Glu Lys Cys Tyr Pro Pro Lys Leu Asp Glu Val Lys Glu
1895                1900                1905

Gln Leu Leu Leu Lys Lys Leu Gln Glu Ser Ala Ser Met Ala Asn
1910                1915                1920

Arg Ser Arg Tyr Gln Ser Arg Lys Val Glu Asn Met Lys Ala Thr
1925                1930                1935

Ile Val Gln Arg Leu Lys Gly Gly Cys Lys Leu Tyr Leu Met Ser
1940                1945                1950

Glu Thr Pro Lys Val Pro Thr Tyr Arg Thr Thr Tyr Pro Ala Pro
1955                1960                1965

Val Tyr Ser Pro Pro Ile Asn Ile Arg Leu Ser Asn Pro Glu Ser
1970                1975                1980

Ala Val Ala Ala Cys Asn Glu Phe Leu Ala Arg Asn Tyr Pro Thr
1985                1990                1995

Val Ala Ser Tyr Gln Ile Thr Asp Glu Tyr Asp Ala Tyr Leu Asp
2000                2005                2010

Met Val Asp Gly Ser Glu Ser Cys Leu Asp Arg Ala Thr Phe Asn
2015                2020                2025

Pro Ser Lys Leu Arg Ser Tyr Pro Lys Gln His Ser Tyr His Ala
2030                2035                2040

Pro Thr Ile Arg Ser Ala Val Pro Ser Pro Phe Gln Asn Thr Leu
2045                2050                2055

Gln Asn Val Leu Ala Ala Ala Thr Lys Arg Asn Cys Asn Val Thr
2060                2065                2070

Gln Met Arg Glu Leu Pro Thr Leu Asp Ser Ala Val Phe Asn Val
2075                2080                2085

Glu Cys Phe Lys Lys Phe Ala Cys Asn Gln Glu Tyr Trp Lys Glu
2090                2095                2100

Phe Ala Ala Ser Pro Ile Arg Ile Thr Thr Glu Asn Leu Thr Thr
2105                2110                2115

Tyr Val Thr Lys Leu Lys Gly Pro Lys Ala Ala Ala Leu Phe Ala
2120                2125                2130

Lys Thr His Asn Leu Leu Pro Leu Gln Glu Val Pro Met Asp Arg
2135                2140                2145

Phe Thr Val Asp Met Lys Arg Asp Val Lys Val Thr Pro Gly Thr
2150                2155                2160

Lys His Thr Glu Glu Arg Pro Lys Val Gln Val Ile Gln Ala Ala
2165                2170                2175

Glu Pro Leu Ala Thr Ala Tyr Leu Cys Gly Ile His Arg Glu Leu
```

```
                2180                2185                2190
Val Arg Arg Leu Asn Ala Val Leu Leu Pro Asn Val His Thr Leu
    2195                2200                2205
Phe Asp Met Ser Ala Glu Asp Phe Asp Ala Ile Ile Ala Ala His
    2210                2215                2220
Phe Lys Pro Gly Asp Ala Val Leu Glu Thr Asp Ile Ala Ser Phe
    2225                2230                2235
Asp Lys Ser Gln Asp Ser Leu Ala Leu Thr Ala Leu Met Leu
    2240                2245                2250
Leu Glu Asp Leu Gly Val Asp His Pro Leu Leu Asp Leu Ile Glu
    2255                2260                2265
Ala Ala Phe Gly Glu Ile Ser Ser Cys His Leu Pro Thr Gly Thr
    2270                2275                2280
Arg Phe Lys Phe Gly Ala Met Met Lys Ser Gly Met Phe Leu Thr
    2285                2290                2295
Leu Phe Val Asn Thr Leu Leu Asn Ile Thr Ile Ala Ser Arg Val
    2300                2305                2310
Leu Glu Asp Arg Leu Thr Arg Ser Ala Cys Ala Ala Phe Ile Gly
    2315                2320                2325
Asp Asp Asn Ile Ile His Gly Val Val Ser Asp Glu Leu Met Ala
    2330                2335                2340
Ala Arg Cys Ala Thr Trp Met Asn Met Glu Val Lys Ile Ile Asp
    2345                2350                2355
Ala Val Val Ser Gln Lys Ala Pro Tyr Phe Cys Gly Gly Phe Ile
    2360                2365                2370
Leu Tyr Asp Thr Val Ala Gly Thr Ala Cys Arg Val Ala Asp Pro
    2375                2380                2385
Leu Lys Arg Leu Phe Lys Leu Gly Lys Pro Leu Ala Ala Gly Asp
    2390                2395                2400
Glu Gln Asp Asp Asp Arg Arg Arg Ala Leu Ala Asp Glu Val Val
    2405                2410                2415
Arg Trp Gln Arg Thr Gly Leu Thr Asp Glu Leu Glu Lys Ala Val
    2420                2425                2430
His Ser Arg Tyr Glu Val Gln Gly Ile Ser Val Val Val Met Ser
    2435                2440                2445
Met Ala Thr Phe Ala Ser Ser Arg Ser Asn Phe Glu Lys Leu Arg
    2450                2455                2460
Gly Pro Val Val Thr Leu Tyr Gly Gly Pro Lys
    2465                2470

<210> SEQ ID NO 23
<211> LENGTH: 1248
<212> TYPE: PRT
<213> ORGANISM: Chikungunya virus

<400> SEQUENCE: 23

Met Glu Phe Ile Pro Thr Gln Thr Phe Tyr Asn Arg Arg Tyr Gln Pro
1               5                   10                  15
Arg Pro Trp Ala Pro Arg Pro Thr Ile Gln Val Ile Arg Pro Arg Pro
            20                  25                  30
Arg Pro Gln Arg Gln Ala Gly Gln Leu Ala Gln Leu Ile Ser Ala Val
        35                  40                  45
Asn Lys Leu Thr Met Arg Ala Val Pro Gln Gln Lys Pro Arg Arg Asn
    50                  55                  60
```

-continued

```
Arg Lys Asn Lys Lys Gln Arg Gln Lys Lys Gln Ala Pro Gln Asn Asp
 65                  70                  75                  80

Pro Lys Gln Lys Lys Gln Pro Pro Gln Lys Lys Pro Ala Gln Lys Lys
                 85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
            115                 120                 125

Leu Val Gly Asp Lys Val Met Lys Pro Ala His Val Lys Gly Thr Ile
        130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
```

-continued

```
                485                 490                 495
Pro Pro Asp Thr Pro Asp Arg Thr Leu Met Thr Gln Gln Ser Gly Asn
            500                 505                 510
Val Lys Ile Thr Val Asn Gly Gln Thr Val Arg Tyr Lys Cys Asn Cys
            515                 520                 525
Gly Gly Ser Asn Glu Gly Leu Thr Thr Thr Asp Lys Val Ile Asn Asn
            530                 535                 540
Cys Lys Ile Asp Gln Cys His Ala Ala Val Thr Asn His Lys Asn Trp
545                 550                 555                 560
Gln Tyr Asn Ser Pro Leu Val Pro Arg Asn Ala Glu Leu Gly Asp Arg
            565                 570                 575
Lys Gly Lys Ile His Ile Pro Phe Pro Leu Ala Asn Val Thr Cys Arg
            580                 585                 590
Val Pro Lys Ala Arg Asn Pro Thr Val Thr Tyr Gly Lys Asn Gln Val
            595                 600                 605
Thr Met Leu Leu Tyr Pro Asp His Pro Thr Leu Leu Ser Tyr Arg Asn
            610                 615                 620
Met Gly Gln Glu Pro Asn Tyr His Glu Glu Trp Val Thr His Lys Lys
625                 630                 635                 640
Glu Val Thr Leu Thr Val Pro Thr Glu Gly Leu Glu Val Thr Trp Gly
            645                 650                 655
Asn Asn Glu Pro Tyr Lys Tyr Trp Pro Gln Met Ser Thr Asn Gly Thr
            660                 665                 670
Ala His Gly His Pro His Glu Ile Ile Leu Tyr Tyr Tyr Glu Leu Tyr
            675                 680                 685
Pro Thr Met Thr Val Val Ile Val Ser Val Ala Ser Phe Val Leu Leu
            690                 695                 700
Ser Met Val Gly Thr Ala Val Gly Met Cys Val Cys Ala Arg Arg Arg
705                 710                 715                 720
Cys Ile Thr Pro Tyr Glu Leu Thr Pro Gly Ala Thr Val Pro Phe Leu
            725                 730                 735
Leu Ser Leu Leu Cys Cys Val Arg Thr Thr Lys Ala Ala Thr Tyr Tyr
            740                 745                 750
Glu Ala Ala Ala Tyr Leu Trp Asn Glu Gln Gln Pro Leu Phe Trp Leu
            755                 760                 765
Gln Ala Leu Ile Pro Leu Ala Ala Leu Ile Val Leu Cys Asn Cys Leu
            770                 775                 780
Lys Leu Leu Pro Cys Cys Cys Lys Thr Leu Ala Phe Leu Ala Val Met
785                 790                 795                 800
Ser Ile Gly Ala His Thr Val Ser Ala Tyr Glu His Val Thr Val Ile
            805                 810                 815
Pro Asn Thr Val Gly Val Pro Tyr Lys Thr Leu Val Asn Arg Pro Gly
            820                 825                 830
Tyr Ser Pro Met Val Leu Glu Met Glu Leu Gln Ser Val Thr Leu Glu
            835                 840                 845
Pro Thr Leu Ser Leu Asp Tyr Ile Thr Cys Glu Tyr Lys Thr Val Ile
            850                 855                 860
Pro Ser Pro Tyr Val Lys Cys Cys Gly Thr Ala Glu Cys Lys Asp Lys
865                 870                 875                 880
Ser Leu Pro Asp Tyr Ser Cys Lys Val Phe Thr Gly Val Tyr Pro Phe
            885                 890                 895
Met Trp Gly Gly Ala Tyr Cys Phe Cys Asp Ala Glu Asn Thr Gln Leu
            900                 905                 910
```

```
Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
        930                 935                 940

Leu Tyr Gln Gly Asn Asn Ile Thr Val Ala Ala Tyr Ala Asn Gly Asp
945                 950                 955                 960

His Ala Val Thr Val Lys Asp Ala Lys Phe Val Val Gly Pro Met Ser
                965                 970                 975

Ser Ala Trp Thr Pro Phe Asp Asn Lys Ile Val Val Tyr Lys Gly Asp
        980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Ala Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080

Asn Ile Pro Ile Ser Ile Asp Ile Pro Asp Ala Ala Phe Thr Arg
    1085                1090                1095

Val Val Asp Ala Pro Ser Val Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Thr Ala Ser Lys Lys Gly Lys Cys Ala Val His Ser Met Thr
    1130                1135                1140

Asn Ala Val Thr Ile Arg Glu Ala Asp Val Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Ala
    1175                1180                1185

Cys His Pro Pro Lys Asp His Ile Val Asn Tyr Pro Ala Ser His
    1190                1195                1200

Thr Thr Leu Gly Val Gln Asp Ile Ser Thr Thr Ala Met Ser Trp
    1205                1210                1215

Val Gln Lys Ile Thr Gly Gly Val Gly Leu Ile Val Ala Val Ala
    1220                1225                1230

Ala Leu Ile Leu Ile Val Val Leu Cys Val Ser Phe Ser Arg His
    1235                1240                1245

<210> SEQ ID NO 24
<211> LENGTH: 20
<212> TYPE: DNA
<213> ORGANISM: Artificial Sequence
<220> FEATURE:
<223> OTHER INFORMATION: Synthetis primer

<400> SEQUENCE: 24
cagtgatccc gaacacggtg                                              20
```

```
<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
ccacataaat gggtagactc c                                              21
```